US008431698B2

(12) United States Patent
Neff et al.

(10) Patent No.: US 8,431,698 B2
(45) Date of Patent: Apr. 30, 2013

(54) BIOLUMINESCENT ENDOSCOPY METHODS AND COMPOUNDS

(75) Inventors: Philip T. Neff, Golden, CO (US); Randall B. Murphy, Glenmoore, PA (US); Bruce Bryan, Beverly Hills, CA (US)

(73) Assignee: BioLume Inc., Morrisville, NC (US)

(*) Notice: Subject to any disclaimer, the term of this patent is extended or adjusted under 35 U.S.C. 154(b) by 331 days.

(21) Appl. No.: 12/201,680

(22) Filed: Aug. 29, 2008

(65) Prior Publication Data

US 2009/0081129 A1    Mar. 26, 2009

Related U.S. Application Data

(60) Provisional application No. 60/968,772, filed on Aug. 29, 2007.

(51) Int. Cl.
*C07D 491/00* (2006.01)
*C07D 495/00* (2006.01)
*C07D 497/00* (2006.01)

(52) U.S. Cl.
USPC ................................ 544/350; 424/9.6; 435/8

(58) Field of Classification Search ............ None
See application file for complete search history.

(56) References Cited

U.S. PATENT DOCUMENTS

| | | | |
|---|---|---|---|
| 2,890,624 A | 6/1959 | Widdop et al. | |
| 4,047,805 A | 9/1977 | Sekimura | |
| 4,832,448 A | 5/1989 | Jones | |
| 4,916,534 A | 4/1990 | Takhashi et al. | |
| 5,360,728 A | 11/1994 | Prasher | |
| 5,374,534 A | 12/1994 | Zomer et al. | |
| 5,400,174 A | 3/1995 | Pagis et al. | |
| 5,422,266 A | 6/1995 | Cormier et al. | |
| 5,541,309 A | 7/1996 | Prasher | |
| 5,583,024 A | 12/1996 | McElroy et al. | |
| 5,674,713 A | 10/1997 | McElroy et al. | |
| 5,741,668 A | 4/1998 | Ward et al. | |
| 5,984,861 A | 11/1999 | Crowley | |
| 5,993,037 A | 11/1999 | Tomioka et al. | |
| 6,217,847 B1 | 4/2001 | Contag et al. | |
| 6,228,604 B1 | 5/2001 | Escher et al. | |
| 6,247,995 B1 | 6/2001 | Bryan | |
| 6,364,829 B1 | 4/2002 | Fulghum | |
| 6,369,964 B1 | 4/2002 | Chang | |
| 6,387,675 B1 | 5/2002 | Wood et al. | |
| 6,416,960 B1 | 7/2002 | Bryan | |
| 6,451,549 B1 | 9/2002 | Escher et al. | |
| 6,458,547 B1 | 10/2002 | Bryan et al. | |
| 6,596,257 B2 | 7/2003 | Bryan | |
| 6,649,143 B1 | 11/2003 | Contag et al. | |
| 6,649,356 B2 | 11/2003 | Bryan et al. | |
| 6,649,357 B2 | 11/2003 | Bryan et al. | |
| 6,682,899 B2 | 1/2004 | Bryan et al. | |
| 6,829,271 B2 | 12/2004 | Sato et al. | |
| 6,890,515 B2 | 5/2005 | Contag et al. | |
| 6,908,605 B2 | 6/2005 | Contag et al. | |
| 6,916,462 B2 | 7/2005 | Contag et al. | |
| 6,939,533 B2 | 9/2005 | Contag et al. | |
| 6,962,986 B2 | 11/2005 | Viviani et al. | |
| 7,109,315 B2 | 9/2006 | Bryan et al. | |
| 7,129,464 B2 | 10/2006 | Buchin | |
| 7,183,092 B2 | 2/2007 | Choi et al. | |
| 7,198,774 B2 | 4/2007 | Contag et al. | |
| 7,199,378 B2 | 4/2007 | Ishiura et al. | |
| 2002/0090659 A1 | 7/2002 | Bryan | |
| 2002/0119542 A1 | 8/2002 | Viviani et al. | |
| 2003/0059798 A1 | 3/2003 | Bryan et al. | |
| 2003/0113741 A1 | 6/2003 | Bryan et al. | |
| 2005/0089964 A1 | 4/2005 | Viviani et al. | |
| 2005/0144661 A1 | 6/2005 | Piwnica-Worms et al. | |
| 2006/0053505 A1 | 3/2006 | Bryan | |
| 2007/0025917 A1 | 2/2007 | Tian et al. | |
| 2007/0042375 A1 | 2/2007 | Golz et al. | |
| 2007/0065818 A1 | 3/2007 | Foti et al. | |
| 2007/0155806 A1 | 7/2007 | Takakura et al. | |
| 2007/0161067 A1 | 7/2007 | Gambhir et al. | |

OTHER PUBLICATIONS

Roth et al. Transplantation. 2006. 1185-1190.*
Dubuisson, et al; "Discovery and Validation of a New Family of Antioxidants: The Aminopyrazine Derivatives"; Mini Reviews in Medicinal Chemistry; 2004; pp. 421-435.
Estourgie, et al; "Lymphatic Drainage Patterns From the Breast"; Annals of Surgery; vol. 239; Feb. 2004; pp. 232-237.
Anctil, et al.; "Mechanism of photoinactivation and re-activation in bioluminescence system of the ctenophpre Mnemiopsis"; Biochem. J. (1984) 269-272.
Fenaroli, et al.; "Population-based sentinel lymph node biopsy in early invasive breast cancer"; The Journal of Cancer Surgery; (2004) pp. 618-623.
Inouye, et al.- "Secretional luciferase of the luminous shrimp Oplophorus gracilirostris: cDNA cloning of a novel imidazopyrazinone luciferase"; FEBS letters 481 (2000); pp. 19-25.
Broekhuizen, et al.; "The incidence and significance of micrometastases in lymph nodes of patients with ductal carcinoma in situ and T1a carcinoma of the breast"; The Journal of Cancer Surgery; (2006); pp. 502-506.

* cited by examiner

*Primary Examiner* — Michael G Hartley
*Assistant Examiner* — Sean R Donohue
(74) *Attorney, Agent, or Firm* — St. Onge Steward Johnston & Reens LLC

(57) ABSTRACT

Bioluminescent endoscopy methods and compounds, wherein an anatomical object is examined by means of filling, perfusing, intubating, injecting, or otherwise administering a solution containing a bioluminescent substance or a mixture of luciferin and luciferase which produces bioluminescence, wherein a color or monochrome image of the object is constituted using the images and information based on bioluminescent emitted by the bioluminescent substance. Procedures are demonstrated which allow bioluminescent solutions to be perfused into certain tissue regions, such as but not limited to the common biliary duct, genitourinary tract, gastro-intestinal tract, cardiovascular system and lymphatic system wherein said structures may be conveniently visualized during surgery to avoid damage to these structures. Such images may also be combined with visual light images. Methods of detection of cancer cells using bioluminescence are provided. Preferred embodiments disclosed include membrane permeant coelenterazine analogs.

22 Claims, 39 Drawing Sheets
(19 of 39 Drawing Sheet(s) Filed in Color)

1-(4-(dec-1-ynyl)phenyl)ethanone 1-(4-(dec-1-ynyl)phenyl)ethanone      2-(1-(4-(dec-1-ynyl)phenyl)ethyl)-1,3-dioxolane Step 1 (prior art)

(literature 88%)

Step 2 (prior art)

(literature 93%)

Step 3 (New)

BIOLUMINESCENT ENDOSCOPY METHODS AND COMPOUNDS

CROSS-REFERENCE TO RELATED APPLICATIONS

The present application claims the benefit under 35 U.S.C. §119(e) of the U.S. Provisional Patent Application Ser. No. 60/968,772, filed on Aug. 29, 2007, the content of which is incorporated herein by reference.

FIELD OF THE INVENTION

The present invention relates to methods and compositions for in vivo endoscopic diagnosis and surgical treatment in a living animal, bird, or man. Specifically, the present invention relates to a bioluminescent endoscopy methods, and compounds for use in bioluminescent endoscopy, by which images may be obtained by the use of appropriate cameras and signal processing algorithms, if necessary, from tissues which contain a bioluminescent compound and/or mixture of compounds which are injected, administered, or by any means whatsoever placed within said tissue.

BACKGROUND OF THE INVENTION

In recent years endoscopes capable of viewing a patient or test subject have been widely employed. An endoscope can observe organs or other structures. Further, an endoscope can be used for providing therapeutic treatments or surgical interventions by inserting treatment tools into a treatment tool channel provided therein. A typical example of this would be a rigid endoscope including a hard insertion section, which incorporates an image capturing device. With this rigid endoscope, a light guide cable and a scope cable are integrated within the rigid endoscope main body. Flexible endoscopes may also be used to observe anatomic structures. Many different types of electronic endoscopes using a solid state imaging device such as a charge coupled device (CCD) or complementary metal-oxide-semiconductor sensor (CMOS) as imaging means have also been considered and/or used.

However, certain anatomical structures are difficult to observe in conventional endoscopes under normal visible lighting conditions. For example, the common bile duct is not infrequently damaged in laparoscopic resection of the gallbladder because of its size, location and visual perception limitations inherent in endoscopic surgical techniques (Way L W, Stewart L, Gantert W, Liu K, Lee C M, Whang K, Hunter J G. "Causes and prevention of laparoscopic bile duct injuries: analysis of 252 cases from a human factors and cognitive psychology perspective." Annals of Surgery 2003 April; 237 (4):460-9). Similarly, the ureter can be damaged in surgery, especially in pelvic operations. Although these injuries can be repaired, they may not be apparent until after the conclusion of the procedure. Commonly in the case of the bile duct, infusion of the duct structures with an X-ray contrast agent may be performed, and an X-ray photograph or fluoroscopic image is taken in the form of an intraoperative cholangiogram. This necessitates stopping the surgical procedure and requires bringing an X-ray machine into the operating theater. Furthermore, the operator and assistants must put on lead gowns making this procedure inconvenient and time consuming. For this reason, many surgeons may be resistant to this X-ray examination. An extensive review on the role of intraoperative cholangiography in avoiding bile duct injury the data suggest that the use and correct interpretation of IOC decreases the rate of common bile duct injury and that its broader use will improve patient safety (Massarweh N N, Flum D R. (2007). "Role of intraoperative cholangiography in avoiding bile duct injury." Journal American College Surgery 204(4):656-64. However, selective intraoperative cholangiography as compared to routine intraoperative cholangiography (IOC) techniques in itself increases the risk of injury to the common bile duct (Flum D R, Dellinger E P, Cheadle A, Chan L, Koepsell T (2003) "Intraoperative cholangiography and risk of common bile duct injury during cholecystectomy." Journal American Medical Association 289(13):1639-44).

As described in more detail herein, the present invention provides for bioluminescent endoscopy methods, and compounds for use in bioluminescent endoscopy, to avoid such problems in surgery. However, and potentially much more significantly, the present invention also has a significant use in the detection and treatment of cancer, including specifically, breast cancer and melanoma.

Radical mastectomy was first demonstrated nearly 100 years ago by Halstead as a potentially effective surgical response to breast cancer. Fifty years later, Patey proved that modified radical mastectomy could yield similar survival with limited morbidity. Since the time of Halstead to the current day, the status of the regional nodal basin remains the single most important independent variable in predicting prognosis. Advocates of axillary dissection contend that there is a benefit for breast cancer patients because axillary dissection provides direct regional control of axillary disease. Axillary lymph node dissection (ALND) provides excellent regional tumor control, and the pathologic information gained is pivotal to the planning of adjuvant therapy. Axillary lymph node metastasis in patients with early breast cancer is the single most important prognostic factor for recurrence and survival and forms the basis for important therapeutic decisions. Critics of axillary dissection maintain that overall survival depends on the development of distant metastases and is not influenced by axillary dissection in most patients. They contend that patients with microscopic axillary metastases might be cured with adjuvant chemotherapy with or without nodal irradiation in the absence of axillary dissection. Many have even advocated abandoning axillary dissection in early breast cancer. Axillary lymph node dissection is a major operation; ALND is associated with acute complication rates of 20% to 30% and chronic lymphedema rates of 7% to 37%. The majority of women who undergo ALND for breast cancer experience enduring surgery-related symptoms such as scarring, pain, numbness, lymphedema and weakness and stiffness of the ipsilateral arm and shoulder, as well as decreased sweat production in the distribution of the intercostobrachial nerve. Postoperative studies have shown that the degree of total pain was significantly associated with the number of lymph nodes dissected. These controversies have been amplified by the fact that the fundamental biology of lymphatic metastasis remains poorly understood. There is as yet an incomplete understanding of functional lymphatic biology, and a general lack of appropriate experimental models (Tanis, P. J., M. C. van Rijk, et al. (2005). "The posterior lymphatic network of the breast rediscovered." *Journal of Surgical Oncology* 91(3): 195-8.; Barrett, T., P. L. Choyke, et al. (2006). "Imaging of the lymphatic system: new horizons." *Contrast Media & Molecular Imaging* 1(6): 230-45.; Estourgie, S. H., O. E. Nieweg, et al. (2004). "Lymphatic drainage patterns from the breast. [see comment]." *Annals of Surgery* 239(2): 232-7.)

Systematic studies in breast cancer have shown that breast cancer spreads via the lymphatic system to one or a few lymph nodes before it spreads to other axillary nodes. These first affected lymph nodes are often labeled as "sentinel lymph node(s)" (SLNs), Sentinel-lymph-node biopsy (SNB) was developed for the axillary staging of breast carcinoma. See Chetty, U., P. K. Chin, et al. (2008). "Combination blue dye sentinel lymph node biopsy and axillary node sampling: the Edinburgh experience." *European Journal of Surgical Oncology* 34(1): 13-6.; Christiansen, P., E. Friis, et al. (2008). "Sentinel node biopsy in breast cancer: five years experience from Denmark." *Acta Oncologica* 47(4): 561-8.; Cochran, A. J., S. J. Ohsie, et al. (2008). "Pathobiology of the sentinel node." *Current Opinion in Oncology* 20(2): 190-5.; Fenaroli, P., M. Merson, et al. (2004). "Population-based sentinel lymph node biopsy in early invasive breast cancer." *European Journal of Surgical Oncology* 30(6): 618-23.

If the SLN does not contain metastasis, then patients and surgeons may choose to delay or omit ALND, with a favorable effect on patients' quality of life. Despite few controlled clinical studies of SNB, this procedure has become widely practiced in the United States, Europe, and Australia. Currently, at most major cancer centers in the United States, SNB is performed without ALND if no disease is found in the SLN. (Bankhead, C. (2007). "Debate over sentinel node biopsy continues." *Journal of the National Cancer Institute* 99(10): 751-3.) The American Society of Clinical Oncology (ASCO) officially supports the use of SNB for staging disease in most women with clinically negative axillary lymph nodes. They continue to recommend routine ALND for patients with a positive SLN according to routine histopathological examination. (Lyman, G. H., A. E. Giuliano, et al. (2005). "American Society of Clinical Oncology guideline recommendations for sentinel lymph node biopsy in early-stage breast cancer. [see comment]." *Journal of Clinical Oncology* 23(30): 7703-20.) SNB is not recommended for large or locally advanced invasive breast cancers (Boileau, J. F., A. Easson, et al. (2008). "Sentinel nodes in breast cancer: relevance of axillary level II nodes and optimal number of nodes that need to be removed." *Annals of Surgical Oncology* 15(6): 1710-6.)

The SNL biopsy is typically evaluated by classical staining methods, or preferably in combination with the immunohistochemical staining of lymph nodes. The histological status of the axillary nodes remains the single best predictor of survival in patients with breast cancer. Ideally, the SNL biopsy would involve intraoperative frozen-section examination, involving complete sectioning of the entire lymph node and examination of a large number of sections. Unfortunately, until quite recently this has been difficult to perform in the intraoperative setting in a definitive manner, and even now, rapid immunohistochemical analysis of the sections remains difficult.

Therefore, various methods for lymphatic imaging have been used during the interoperative procedures. Lymphatic connection with the tumor can be identified by using Lymphazurin vital blue dye, various other vital stains, a radiolabeled colloid, or a combination thereof. Indeed, the greatest proportion of successful mappings and the lowest false-negative rates were associated with studies in which both blue dye and radiolabeled colloid were used. (Kitai, T., T. Inomoto, et al. (2005). "Fluorescence navigation with indocyanine green for detecting sentinel lymph nodes in breast cancer." *Breast Cancer* 12(3): 211-5.; Koizumi, M., E. Nomura, et al. (2004). "Radioguided sentinel node detection in breast cancer patients: comparison of 99 $mT_c$ phytate and $99^mT_c$ rhenium colloid efficacy." *Nuclear Medicine Communications* 25(10): 1031-7.; Anan, K., S. Mitsuyama, et al. (2006). "Double mapping with subareolar blue dye and peritumoral green dye injections decreases the false-negative rate of dye-only sentinel node biopsy for early breast cancer: 2-site injection is more accurate than 1-site injection. [see comment]." *Surgery* 139(5): 624-9; Lin, K. M., T. H. Patel, et al. (2004). "Intradermal radioisotope is superior to peritumoral blue dye or radioisotope in identifying breast cancer sentinel nodes." *Journal of the American College of Surgeons* 199(4): 561-6; Mariani, G., P. Erba, et al. (2004).; "Lymphoscintigraphic and intraoperative detection of the sentinel lymph node in breast cancer patients: the nuclear medicine perspective." *Journal of Surgical Oncology* 85(3): 112-22.; Nour, A. (2004). "Efficacy of methylene blue dye in localization of sentinel lymph node in breast cancer patients." *Breast Journal* 10(5): 388-91;

In some medical centers, lymphoscintigraphic imaging using a gamma camera is routinely performed before intraoperative probe detection of radioactivity in sentinel nodes at surgery for axillary staging of breast cancer, typically with $^{99m}Tc$ sulfur colloid agents. This is not always easy to do. There is substantial variability in the frequency of imaging visualization of internal mammary nodes, ranging from under 10% to nearly 40% in some series. See Celebioglu, F., L. Perbeck, et al. (2007). "Lymph drainage studied by lymphoscintigraphy in the arms after sentinel node biopsy compared with axillary lymph node dissection following conservative breast cancer surgery." *Acta Radiologica* 48(5): 488-95.). PET scanning has been employed (Zornoza, G., M. J. Garcia-Velloso, et al. (2004). "$^{18}F$-FDG PET complemented with sentinel lymph node biopsy in the detection of axillary involvement in breast cancer." *European Journal of Surgical Oncology* 30(1): 15-9). The frequency of internal mammary nodal visualization may be dependent on the type of colloid used and route of injection as well as the time from imaging until injection (Barranger, E., A. Cortez, et al. (2004). "Laparoscopic sentinel node procedure using a combination of patent blue and radiocolloid in women with endometrial cancer." *Annals of Surgical Oncology* 11(3): 344-9.; Barranger, E., K. Kerrou, et al. (2007). "Place of a hand-held gamma camera (POCI) in the breast cancer sentinel node biopsy." *Breast* 16(5): 443-4.)

In SNB, pathologists receive either single lymph nodes dissected free of fat or axillary fat containing one or more lymph nodes. Fatty nodules are carefully dissected to identify all lymph nodes. Lymph nodes are inspected for blue dye color, if such dye has been used, measured, and cut into sections generally no thicker than 2.0 mm through and parallel to the longest meridian. Each SLN is submitted in a separate cassette or identified by colored ink to permit accurate assessment of the total number of lymph nodes and number of involved lymph nodes; all node sections are submitted for microscopic examination. Radioactivity is quantified in the samples in each cassette if a radioactive tracer has been used.

The sentinel node concept has also been validated in malignant melanoma (Chakera, A. H., K. T. Drzewiecki, et al. (2004). "Sentinel node biopsy for melanoma: a study of 241 patients." *Melanoma Research* 14(6): 521-6; Gipponi, M., C. Di Somma, et al. (2004). "Sentinel lymph node biopsy in patients with Stage I/II melanoma: Clinical experience and literature review." *Journal of Surgical Oncology* 85(3): 133-40. Essner, R. (2006). "Experimental frontiers for clinical applications: novel approaches to understanding mechanisms of lymph node metastases in melanoma." *Cancer & Metastasis Reviews* 25(2): 257-67).

The sentinel node concept has potential application in other types of cancer, due to the known fact that the lymphatic system serves as a primary route for the dissemination of many solid tumors, particularly those of epithelial origin including colon and prostate. The feasibility and diagnostic reliability of sentinel node mapping of lung cancers is currently under study by a number of investigators. (Bustos, M. E., J. J. Camargo, et al. (2008). "Intraoperative detection of sentinel lymph nodes using Patent Blue V in non-small cell lung cancer." *Minerva Chirurgica* 63(1): 29-36.), gynecological (Ayhan, A., H. Celik, et al. (2008). "Lymphatic mapping and sentinel node biopsy in gynecological cancers: a critical review of the literature." *World Journal of Surgical Oncology* 6: 53) and gastrointestinal cancers (Arigami, T., S, Natsugoe, et al. (2006). "Evaluation of sentinel node concept in gastric cancer based on lymph node micrometastasis determined by reverse transcription-polymerase chain Mutter, D., F. Rubino, et al. (2004). "A new device for sentinel node detection in laparoscopic colon resection." *Journal of the Society of Laparoendoscopic Surgeons* 8(4): 347-51. Mayinger, B. (2004). "Endoscopic fluorescence spectroscopic imaging in the gastrointestinal tract." *Gastrointestinal Endoscopy Clinics of North America* 14(3): 487-505.; Mayinger, B., M. Jordan, et al. (2004). "Evaluation of in vivo endoscopic autofluorescence spectroscopy in gastric cancer." *Gastrointestinal Endoscopy* 59(2): 191-8. Ishizaki, M., A. Kurita, et al. (2006). "Evaluation of sentinel node identification with isosulfan blue in gastric cancer." *European Journal of Surgical Oncology* 32(2): 191-6.; Ishikawa, K., K. Yasuda, et al. (2007). "Laparoscopic sentinel node navigation achieved by infrared ray electronic endoscopy system in patients with gastric cancer." *Surgical Endoscopy* 21(7): 1131-4).

SUMMARY OF THE INVENTION

We have found that instillation of a bioluminescent solution into the bile duct, intestinal anastomosis, or ureter during surgery allows excellent instantaneous visualization to the surgeon, potentially preventing damage to these structures. These techniques may also facilitate recognition of leaks or injuries, greatly expediting the surgical procedure. This visualization may be performed using a conventional endoscope or in some methods a modified cooled CCD or CMOS camera specifically adapted for these procedure. These methods are not limited to the above examples, but rather can be applied to any anatomic tube, duct, lumen, vessel, chamber or hollow structure.

We have further found that sentinel node analysis may be performed utilizing coelenterazine and membrane permeant analogs of coelenterazine can be used for the bioluminescent analysis of lymphatic connection to the sentinel node of a tumor. To do this, the enzyme luciferase, typically but not limited to that from *Renilla reniformis*, is injected into the lymphatics which surround the tumor in the manner that technetium colloid or blue dye is administered. Then, upon biopsy of the sentinel node, the biopsy specimen is treated with coelenterazine or a membrane permeant analog of coelenterazine. Bioluminescence may be detected using a camera or a luminometer or by visual inspection.

The present invention further comprises specific compositions, namely membrane permeant analogs of coelenterazine useful in the above methods, and methods of making such membrane permeant coelenterazine analog compositions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

A. Definitions

Figure 1:
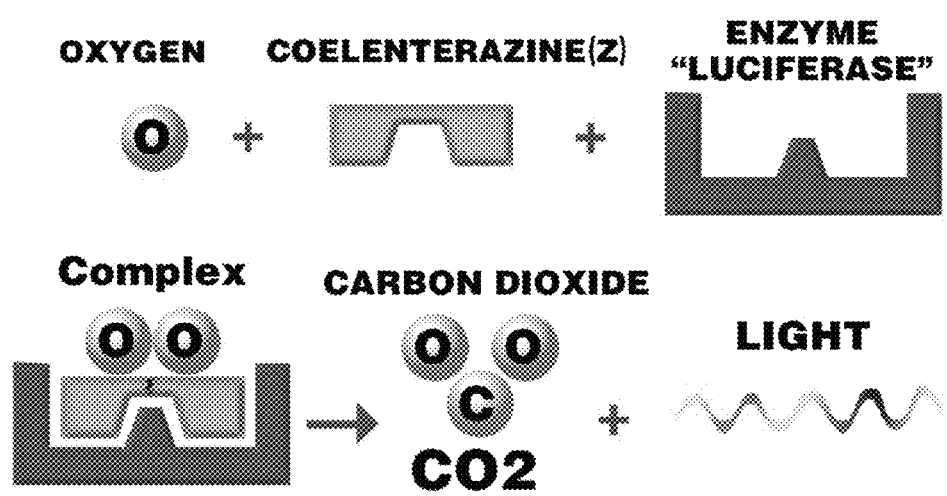
FIG. 1 is a schematic illustration of the process of bioluminescence by oxidation of coelenterazine.

Unless defined otherwise, all technical and scientific terms used herein have the same meaning as is commonly understood by one of skill in the art to which this invention belongs. All patents and publications of referred to herein are incorporated by reference in their entirety.

As used herein, "chemiluminescence" refers to a chemical reaction in which energy is specifically channeled to a molecule causing it to become electronically excited and subsequently to release a photon thereby emitting visible light. Temperature does not contribute to this channeled energy. Thus, chemiluminescence involves the direct conversion of chemical energy to light energy.

As used herein, "luminescence" refers to the detectable electromagnetic radiation, generally, UV, IR or visible light radiation that is produced when the excited product of an exergic chemical process reverts to its ground state with the emission of light. Chemiluminescence is luminescence that results from a chemical reaction. Bioluminescence is chemiluminescence that results from a chemical reaction using biological molecules or synthetic versions or analogs thereof as substrates and/or enzymes.

As used herein, "bioluminescence," which is a type of chemiluminescence, refers to the emission of light by biological molecules, particularly proteins. The essential condition for bioluminescence is molecular oxygen, either bound or free in the presence of an oxygenase, a luciferase, which acts on a substrate, a luciferin. Bioluminescence is generated by an enzyme or other protein (luciferase) that is an oxygenase that acts on a substrate luciferin (a bioluminescence substrate) in the presence of molecular oxygen and transforms the substrate to an excited state, which upon return to a lower energy level releases the energy in the form of detectable electromagnetic radiation.

As used herein, the substrates and enzymes for producing bioluminescence are generically referred to as "luciferin" and "luciferase", respectively. The luciferases and luciferin, activators and other factors, such as $O_2$, $Mg^{++}$, $Ca^{++}$ are referred to as "bioluminescence generating reagents", "agents", or "components." Typically, a subset of these reagents will be provided or combined with an article of manufacture. When reference is made to a particular species thereof, for clarity, each generic term is used with the name of the organism from which it derives, for example, bacterial luciferin or firefly luciferase.

"Luciferase" refers to oxygenases that catalyze a light emitting reaction. For instance, bacterial luciferases catalyze the oxidation of flavin mononucleotide [FMN] and aliphatic aldehydes, which reaction produces light. Another class of luciferases, found among marine arthropods, catalyzes the oxidation of *Cypridina* (also known as *Vargula*) luciferin, and another class of luciferases catalyzes the oxidation of Coleoptera luciferin. Thus, luciferase refers to an enzyme or photoprotein that catalyzes a bioluminescent reaction (a reaction that produces bioluminescence). Luciferase enzymes such as firefly and *Renilla* luciferases act catalytically and are unchanged during the bioluminescence generating reaction. Luciferase photoproteins, such as the aequorin photoprotein to which luciferin is non-covalently bound, are changed, such as by release of the luciferin, during bioluminescence generating reaction. Luciferases employed in the present invention are proteins that occur naturally in an organism, and also variants or mutants thereof, such as a variant produced by mutagenesis that has one or more properties, such as thermal stability, that differ from the naturally-occurring protein. Luciferases and modified mutant or variant forms thereof are well known. For purposes of this application, reference to luciferase refers to either or both luciferase enzymes and photoproteins and their mutant, variant, and synthetic forms. Thus, reference, for example, to "*Renilla* luciferase" means an enzyme isolated from member of the genus *Renilla* or an equivalent molecule obtained from any other source, such as from another Anthozoa, or that has been prepared synthetically.

Bioluminescence is produced upon contacting the combination of and luciferin and any activators, factors or reagents. Bioluminescence has been used for quantitative determinations of specific substances in biology and medicine. For example, luciferase genes have been cloned and exploited as reporter genes in numerous assays, for many purposes. Since the different luciferase systems have different specific requirements, they may be used to detect and quantify a variety of substances.

As used herein, "not strictly catalytically" means that the photoprotein acts as a catalyst to promote the oxidation of the substrate, but it is changed in the reaction, since the bound substrate is oxidized and bound molecular oxygen is used in the reaction. Such photoproteins are regenerated by addition of the substrate and molecular oxygen under appropriate conditions known to those of skill in this art.

As used herein, "bioluminescence substrate" refers to the compound that is oxidized in the presence of a luciferase, and any necessary activators, and generates light. These substrates, referred to as "luciferin" herein, are substrates that undergo oxidation in a bioluminescence reaction. These bioluminescence substrates include any luciferin or analog thereof or any synthetic compound with which a luciferase interacts to generate light. Preferred substrates are those that are oxidized in the presence of a luciferase or protein in a light-generating reaction. Bioluminescence substrates, thus, include those compounds that those of skill in the art recognize as luciferins. Luciferins, for example, include firefly luciferin, *Cypridina* (also known as *Vargula*) luciferin (coelenterazine), bacterial luciferin, as well as synthetic analogs of these substrates or other compounds that are oxidized in the presence of a luciferase in a reaction the produces bioluminescence.

As used herein, "capable of conversion" into a bioluminescence substrate means susceptible to chemical reaction, such as oxidation or reduction, that yields a bioluminescence substrate. For example, the luminescence producing reaction of bioluminescent bacteria involves the reduction of a flavin mononucleotide group (FMN) to reduced flavin mononucleotide (FMNH$_2$) by a flavin reductase enzyme. The reduced flavin mononucleotide [substrate] then reacts with oxygen [an activator] and bacterial luciferase to form an intermediate peroxy flavin that undergoes further reaction, in the presence of a long-chain aldehyde, to generate light. With respect to this reaction, the reduced flavin and the long chain aldehyde are substrates.

As used herein, "bioluminescence system" or "bioluminescence generating system" refers to the set of reagents required to conduct a bioluminescent reaction. Thus, the specific luciferase, luciferin and other substrates, solvents and other reagents that may be required to complete a bioluminescent reaction form a bioluminescence system. Thus a bioluminescence system refers to any set of reagents that, under appropriate reaction conditions, yield bioluminescence. In general, bioluminescence systems include a bioluminescence substrate, luciferin, a luciferase, which includes enzyme luciferases and photoproteins, and one or more activators. A photoprotein combines a luciferin, a cofactor such as oxygen, and a catalyzing protein (equivalent to a luciferase.). A specific bioluminescence system may be identified by reference to the specific organism from which the luciferase derives; for example, the *Vargula* [also called *Cypridina*] bioluminescence system (or *Vargula* system) includes a *Vargula* luciferase, such as a luciferase isolated from the ostracod, *Vargula* or produced using recombinant means or modifications of these luciferases. This system would also include the particular activators necessary to complete the bioluminescence reaction, such as oxygen and a substrate with which the luciferase reacts in the presence of the oxygen to produce light.

"Appropriate reaction conditions" refers to the conditions necessary for a bioluminescence reaction to occur, such as pH, salt concentrations and temperature.

As used herein, a "surgical viewing" refers to any procedure in which an opening is made in the body of an subject. Such procedures include traditional human and animal surgeries and diagnostic procedures, such as but not limited to laparoscopy, thoracoscopy and arthroscopy procedures. Surgical viewing also refers to any procedure in which a natural orifice is accessed or obturated with a rigid or flexible scope such as but not limited to esophago-gastro-duodenoscopy, colonoscopy or bronchoscopy. Surgical viewing also refers to any angiography, venography, lymphangiography where vessels or tissue beds are cannulated or injected, such as but not limited to diagnostic mapping or completion intraoperative angiography for testing and verification of patency, integrity (leak), or arteriovenous fistula status. Surgical viewing also refers to open operations that do not typically employ an endoscope, rather benefit from a camera and open lens not inserted into a surgical opening or natural orifice, but positioned within close focal length of the operative field for anatomic structure identification. Surgical viewing also refers to open or micro-access operations employing a surgical microscope, such as but not limited to nervous system tumor resections Finally, surgical viewing refers to visualization with the naked eye alone.

As used herein, "Bioluminescence Enhanced Surgical Technology" ("BEST") refers to any combination of techniques or methods that use a bioluminescence generating system with an optical system that thus provides for improved surgical viewing, as defined above. It is anticipated that depending on the specific anatomical structure that is the subject of this bioluminescence enhancement, including but not limited to tubes, ducts, lumens, chambers, vessels and hollow organs, different bioluminescence generating systems will be chosen. Similarly, depending on the specific anatomical structure, different technologies for surgical viewing will be chosen. This technology may range from but is not limited to the surgeon's naked eye, to the various endoscopes, open lens cameras and microscopes, as defined above. This technology may also include use of various filters such as but not limited to a blue-green wavelength filter for the endoscope visualizing the bioluminescence enhanced image and a red filter for selective background illumination of the operative field. Similarly, this technology may include any post image capture processing algorithms used to enhance the analog or digital images obtained, such as but not limited to processing by digital imaging computer software programs. This technology may range from but is not limited to simple refinement of the image, to fusion of 2 or more images in a composite still or movie format.

Amino acids which occur in the various amino acid sequences appearing herein are identified according to their well-known, three-letter or one-letter abbreviations. The nucleotides, which occur in the various DNA fragments, are designated with the standard single-letter designations used routinely in the art. ATP, AMP, NAD$^+$ and NADH refer to adenosine triphosphate, adenosine monophosphate, nicotinamide adenine dinucleotide (oxidized form) and nicotinamide adenine dinucleotide (reduced form), respectively.

As used herein, "production by recombinant" means by using recombinant DNA methods means the use of the well known methods of molecular biology for expressing proteins encoded by cloned DNA. Such expression may be carried out in a bacterial system, such as *E. Coli*, in a mammalian cell line, in yeast or another plant cell line, or in an insect cell line using a baculovirus vector, (see U.S. Pat. No. 6,814,963, Baculovirus Based Expression System, Nov. 9, 2004).

As used herein, "substantially identical" to a product means sufficiently similar so that the property of interest is sufficiently unchanged so that the substantially identical product can be used in place of the product.

The present invention is intended to include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}$C, $^{13}$C, and $^{14}$C.

Certain compounds are described herein using a general formula that includes variables, e.g. B, $R_1$, $R_2$, $R_3$, $R_4$, $R_5$, $R_6$, and $R_7$. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. Also, combinations of substituents and/or variables are permissible only if such combinations result in stable compounds. When a group is substituted by an "oxo" substituent a carbonyl bond replaces two hydrogen atoms on a carbon. An "oxo" substituent on an aromatic group or heteroaromatic group destroys the aromatic character of that group, e.g. a pyridyl substituted with oxo is a pyridone.

The term "substituted", as used herein, means that any one or more hydrogens on the designated atom or group is replaced with a selection from the indicated group, provided that the designated atom's normal valence is not exceeded. When a substituent is oxo (i.e., =O), then two hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent. Unless otherwise specified substituents are named into the core structure. For example, it is to be understood that when (cycloalkyl)alkyl is listed as a possible substituent the point of attachment of this substituent to the core structure is in the alkyl portion.

The phrase "optionally substituted" indicates that such groups may either be unsubstituted or substituted at one or more of any of the available positions, typically 1, 2, 3, or 4 positions, by one or more suitable groups such as those disclosed herein.

Suitable groups that may be present on a "substituted" position include, but are not limited to, e.g., halogen; cyano; hydroxyl; azido; alkanoyl (such as a $C_2$-$C_6$ alkanoyl group such as acyl or the like); carboxamido; alkyl groups (including cycloalkyl groups, having 1 to about 8 carbon atoms, or 1 to about 6 carbon atoms); alkenyl and alkynyl groups (including groups having one or more unsaturated linkages and from 2 to about 8, or 2 to about 6 carbon atoms); alkoxy groups having one or more oxygen linkages and from 1 to about 8, or from 1 to about 6 carbon atoms; aryloxy such as phenoxy; alkylthio groups including those having one or more thioether linkages and from 1 to about 8 carbon atoms, or from 1 to about 6 carbon atoms; alkylsulfinyl groups including those having one or more sulfinyl linkages and from 1 to about 8 carbon atoms, or from 1 to about 6 carbon atoms; alkylsulfonyl groups including those having one or more sulfonyl linkages and from 1 to about 8 carbon atoms, or from 1 to about 6 carbon atoms; aminoalkyl groups including groups having one or more N atoms and from 1 to about 8, or from 1 to about 6 carbon atoms; aryl having 6 or more carbons and one or more rings, (e.g., phenyl, biphenyl, naphthyl, or the like, each ring either substituted or unsubstituted aromatic); arylalkyl having 1 to 3 separate or fused rings and from 6 to about 18 ring carbon atoms, with benzyl being an exemplary arylalkyl group; arylalkoxy having 1 to 3 separate or fused rings and from 6 to about 18 ring carbon atoms, with benzyloxy being an exemplary arylalkoxy group; or a saturated, unsaturated, or aromatic heterocyclic group having 1 to 3 separate or fused rings with 3 to about 8 members per ring and one or more N, O or S atoms, e.g. coumarinyl, quinolinyl, isoquinolinyl, quinazolinyl, pyridyl, pyrazinyl, pyrimidinyl, furanyl, pyrrolyl, thienyl, thiazolyl, triazinyl, oxazolyl, isoxazolyl, imidazolyl, indolyl, benzofuranyl, benzothiazolyl, tetrahydrofuranyl, tetrahydropyranyl, piperidinyl, morpholinyl, piperazinyl, and pyrrolidinyl. Such heterocyclic groups may be further substituted, e.g. with hydroxy, alkyl, alkoxy, halogen and amino.

The exception to naming substituents into the ring is when the substituted atom is listed with a dash ("-") or double bond ("=") that is not between two letters or symbols. In that case the dash or double bond symbol is used to indicate a point of attachment for a substituent. For example, —$CONH_2$ is attached via a single covalent bond through the carbon atom.

As used herein, "alkyl" is intended to include both branched and straight-chain saturated aliphatic hydrocarbon groups, having the specified number of carbon atoms. Thus, the term $C_1$-$C_6$ alkyl as used herein includes alkyl groups having from 1 to about 6 carbon atoms. When $C_0$-$C_n$ alkyl is used herein in conjunction with another group, for example, (aryl)$C_0$-$C_2$ alkyl, the indicated group, in this case aryl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl.

"Alkenyl" as used herein, indicates a hydrocarbon chain of either a straight or branched configuration having one or more carbon-carbon double bond bonds, which may occur at any stable point along the chain. Examples of alkenyl groups include ethenyl and propenyl.

"Alkynyl" as used herein, indicates a hydrocarbon chain of either a straight or branched configuration having one or more triple carbon-carbon bonds that may occur in any stable point along the chain, such as ethynyl and propynyl.

"Alkoxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy, and 3-methylpentoxy.

"Alkanoyl" indicates an alkyl group as defined above, attached through a keto (—(C=O)—) bridge. Alkanoyl groups have the indicated number of carbon atoms, with the carbon of the keto group being included in the numbered carbon atoms. For example a $C_2$: alkanoyl group is an acetyl group having the formula $CH_3$(C=O)—.

As used herein, the terms "mono- or di-alkylamino" or "mono- and di-alkylamino" indicate secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino. A mono- or di-($C_3$-$C_7$cycloalkylamino)$C_0$-$C_2$alkylamino group is an alkyl amino substituent in which a first alkyl group is chosen from $C_3$-$C_7$alkyl and an second alkyl group is chosen from $C_0$-$C_2$alkyl, wherein $C_0$ indicates the absence of a second alkyl group, i.e. a mono-$C_3$-$C_7$alkylamino. The point of attachment to the core structure is on the second, $C_0$-$C_2$alkyl group.

The term "alkylthio" indicates an alkyl group as defined above attached through a sulfur linkage, i.e. a group of the formula alkyl-S—. Examples include ethylthio and pentylthio.

As used herein, the term "aminoalkyl" indicates an alkyl group as defined above substituted with at least one amino substituent. Similarly, the term "hydroxyalkyl" indicates an alkyl group as defined above, substituted with at least one hydroxyl substituent. In certain instances the alkyl group of the aminoalkyl or hydroxyalkyl group may be further substituted.

As used herein, the term "aryl" indicates aromatic groups containing only carbon in the aromatic ring or rings. Typical aryl groups contain 1 to 3 separate, fused, or pendant rings and from 6 to about 18 ring atoms, without heteroatoms as ring members. When indicated, such aryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a 3,4-methylenedioxy-phenyl group. Aryl groups include, for example, phenyl, naphthyl, including 1-naphthyl and 2-naphthyl, and biphenyl In the term "(aryl)alkyl", aryl and alkyl are as defined above, and the point of attachment is on the alkyl group. This term encompasses, but is not limited to, benzyl, phenylethyl, and piperonyl. Similarly, in the terms (aryl)alkoxy and (aryl) alkylthio, aryl, alkylthio, and alkoxy are as defined above and the point of attachment is through the oxygen atom of the alkoxy group or the sulfur group of the alkylthio. If the alkoxy is a $C_0$ alkoxy the aryl is attached through an oxygen bridge; if the alkylthio is a $C_0$alkylthio the aryl is attached through the sulfur. Likewise (aryl)alkyl(C=O)— is an arylalkyl attached to the core structure through a keto group.

"Cycloalkyl" as used herein, indicates saturated hydrocarbon ring groups, having the specified number of carbon atoms, usually from 3 to about 8 ring carbon atoms, or from 3 to about 7 carbon atoms. Examples of cycloalkyl groups include cyclopropyl, cyclobutyl, cyclopentyl, or cyclohexyl as well as bridged or caged saturated ring groups such as norborane or adamantane, and cubane.

In the terms "(cycloalkyl)alkyl," and "(cycloalkyl)alkoxy" the terms cycloalkyl, alkyl, carbohydryl, and alkoxy are as defined above, and the point of attachment is on the alkyl, carbohydryl, or alkoxy group respectively. These terms include examples such as cyclopropylmethyl, cyclohexylmethyl, cyclohexylpropenyl, and cyclopentylethyoxy.

The term "(cycloalkyl)alkylamino" indicates an amino group substituted with at least one (cycloalkyl)alkyl or cycloalkyl (when the alkyl is a $C_0$ alkyl). The amino group may be a secondary, in which case the other nitrogen atom valence is occupied by a hydrogen atom or a tertiary amino wherein containing an additional alkyl or (cycloalkyl)alkyl substituent.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge. Examples of haloalkoxy include, but are not limited to, trifluoromethoxy, difluoromethoxy, 2-fluoroethyoxy, and pentafluoroethoxy. Halo" or "halogen" as used herein includes fluoro, chloro, bromo, and iodo.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein "equivalent," when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions that do not substantially alter the activity or function of the protein or peptide. When "equivalent" refers to a property, the property does not need to be present to the same extent (e.g., two peptides can exhibit different rates of the same type of enzymatic activity), but the activities are preferably substantially the same.

"Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

The term "substantially" identical or homologous or similar varies with the context as understood by those skilled in the relevant art and generally means at least 70%, preferably means at least 80%, more preferably at least 90%, and most preferably at least 95% identity.

As used herein, "biological activity" refers to the in vivo activities of a compound or physiological responses that result upon administration of a compound, composition or other mixture. Biological activities may be observed in vitro systems designed to test or use such activities. Thus, for purposes herein the biological activity of a luciferase is its oxygenase activity whereby, upon oxidation of a substrate, light is produced.

As used herein, a "composition" refers to any mixture. It may be a solution, a suspension, liquid, powder, a paste, aqueous, non-aqueous or any combination thereof.

As used herein, a "combination" refers to any association between two or among more items.

As used herein, "fluid" refers to any composition that can flow. Fluids thus encompass compositions that are in the form of semi-solids, pastes, solutions, aqueous mixtures, gels, lotions, creams and other such compositions.

B. Bioluminescence

Luminescence is a phenomenon in which energy is specifically channeled to a molecule to produce an excited state. Return to a lower energy state is accompanied by release of a photon (hv). Luminescence includes fluorescence, phosphorescence, chemiluminescence and bioluminescence. Bioluminescence is the process by which living organisms emit light that is visible to other organisms. Luminescence may be represented as follows:

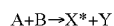

$$A+B \rightarrow X^*+Y$$

$$X^* \rightarrow X+h\nu$$

Where X* is an electronically excited molecule and hv represents light emission upon return of X* to a lower energy state. Where the luminescence is bioluminescence, creation of the excited state derives from an enzyme catalyzed reaction. The color of the emitted light in a bioluminescent (or chemiluminescent or other luminescent) reaction is characteristic of the excited molecule, and is independent from its source of excitation and temperature.

Though rare overall, bioluminescence is more common in marine organisms than in terrestrial organisms. Bioluminescence has developed from as many as thirty evolutionarily distinct origins and, thus, is manifested in a variety of ways so that the biochemical and physiological mechanisms responsible for bioluminescence in different organisms are distinct. Bioluminescent species span many genera and include microscopic organisms, such as bacteria (primarily marine bacteria including *Vibrio* species), fungi, algae and dinoflagellates, to marine organisms, including arthropods, mollusks, echinoderms, and chordates, and terrestrial organism including annelid worms and insects.

C. Bioluminescence Generating Systems

A bioluminescence generating system includes the components that are necessary and sufficient to generate bioluminescence. These include a luciferase, luciferin and any necessary co-factors or conditions. Virtually any bioluminescent system known to those of skill in the art will be amenable to use in the methods provided herein.

In general, bioluminescence refers to an energy-yielding chemical reaction in which a specific chemical substrate, a luciferin, undergoes oxidation, catalyzed by an enzyme, a luciferase. An essential condition for bioluminescence is the use of molecular oxygen, either bound or free in the presence of a luciferase. Luciferases, are oxygenases, which act on the substrate, luciferin, in the presence of molecular oxygen and transform the substrate to an excited state. Upon return to a lower energy level, energy is released in the form of light. This process is illustrated in FIG. 1: The oxidized reaction product is termed oxyluciferin, and certain luciferin precursors are termed etioluciferin. Thus, for purposes herein bioluminescence encompasses light produced by reactions that are catalyzed by (in the case of luciferases that act enzymatically) or initiated by (in the case of the photoproteins, such as aequorin, that are not regenerated in the reaction) a biological protein or analog, derivative or mutant thereof. Bioluminescent reactions are easily maintained, requiring only replenishment of exhausted luciferin or other substrate or cofactor or other protein, in order to continue or revive the reaction. Bioluminescent generating reactions are well-known to those of skill in this art and any such reaction may be adapted for use in combination with articles of manufacture as described herein.

Luciferases include enzymes such as the luciferases that catalyze the oxidation of luciferin, emitting light and releasing oxyluciferin. Also included among luciferases are photoproteins, which catalyze the oxidation of luciferin to emit light but are changed in the reaction and must be reconstituted to be used again. The luciferases may be naturally occurring or may be modified, such as by genetic engineering to improve or alter certain properties. As long as the resulting molecule retains the ability to catalyze the bioluminescent reaction, it is encompassed herein.

Any protein that has luciferase activity (catalysis of oxidation of a substrate in the presence of molecular oxygen to produce light as defined herein) may be used herein. The preferred luciferases are those that are described herein or that have minor sequence variations. Such minor sequence variations include, but are not limited to, minor allelic or species variations and insertions or deletions of residues, particularly cysteine residues. Suitable conservative substitutions of amino acids are known to those of skill in this art and may be made generally without altering the biological activity of the resulting molecule. Those of skill in this art recognize that, in general, single amino acid substitutions in non-essential regions of a polypeptide do not substantially alter biological activity. Other substitutions are also permissible and may be determined empirically or in accord with known conservative substitutions. Any such modification of the polypeptide may be effected by any means known to those of skill in this art.

It is understood that a bioluminescence generating system may be isolated from natural sources, or may be produced synthetically. In addition, for uses herein, the components need only be sufficiently pure so that mixture thereof, under appropriate reaction conditions, produces a glow so that cells and tissues can be visualized during a surgical procedure. Thus, in some embodiments, a crude extract or merely grinding up the organism may be adequate. Generally, however, substantially pure components are used. Also, components may be synthetic components that are not isolated from natural sources. DNA encoding luciferases is and synthetic and alternative substrates have been devised. Any bioluminescence generating system, whether synthetic or isolated from natural sources, is intended for use in the methods provided herein. The luciferases may be obtained commercially, isolated from natural sources, expressed in host cells using DNA encoding the luciferase, or obtained in any manner known to those of skill in the art. The luciferin substrates for the reaction or for inclusion in the conjugates include any molecule(s) with which the luciferase reacts to produce light. Such molecules include the naturally-occurring substrates, modified forms thereof, and synthetic analogues.

There are numerous organisms and sources of bioluminescence generating systems, and some representative genera and species that exhibit bioluminescence are set forth in Hastings, in (1995) Cell Physiology: Source Book, N. Sperelakis (ed.), Academic Press, pp 665-681]. Other bioluminescent organisms contemplated for use herein are *Gonadostomias, Gaussia, Watensia, Halisturia*, Vampire squid, *Glyphus*, Mycotophids (a fish), *Vinciguerria, Howella, Florenciella, Chaudiodus, Melanocostus* and Sea Pens.

Examples of luciferases include, but are not limited to, those isolated from the ctenophores *Mnemiopsis* (mnemiopsin) and *Beroe ovata*(berovin), those isolated from the coelenterates *Aequorea* (aequorin), Obelia (obelin), *Pelagia*, the *Renilla* luciferase, the luciferases isolated from the mollusca *Pholas* (pholasin), the luciferases isolated from fish, such as *Aristostomias, Pachystomias* and *Poricthys* and from the ostracods, such as *Cypridina* (also referred to as *Vargula*).

The majority of commercial bioluminescence applications are based on firefly luciferase [*Photinus pyralis*]. One of the first and still widely used assays involves the use of firefly luciferase to detect the presence of ATP. It is also used to detect and quantify other substrates or co-factors in the reaction. Any reaction that produces or utilizes NAD(H), NADP (H) or long chain aldehyde, either directly or indirectly, can be coupled to the light-emitting reaction of bacterial luciferase.

Another luciferase system that has been used commercially for analytical purposes is the Aequorin photoprotein system. The purified jellyfish photoprotein, aequorin, is used to detect and quantify intracellular $Ca^{++}$ and its changes under various experimental conditions. The Aequorin is relatively small [about 20 kDa], nontoxic, and can be injected into cells in quantities adequate to detect calcium over a large concentration range [$3\times10^{-7}$ to $10^{-4}$ M].

Because of their analytical utility, many luciferases and substrates have been studied and well-characterized and are commercially available. Firefly luciferase is available from Sigma, St. Louis, Mo., and Boehringer Mannheim Biochemicals, Indianapolis, Ind.; recombinantly produced firefly luciferase and other reagents based on this gene or for use with this protein are available from Promega Corporation, Madison, Wis.; the aequorin photoprotein luciferase from jellyfish and luciferase from *Renilla* are commercially available from Prolume, Inc. (Pinetop, Ariz.); coelenterazine, the naturally-occurring substrate for these luciferases, is available from Invitrogen Molecular Probes (Carlsbad, Calif.) and Prolume, Inc. (Pinetop, Ariz.). These luciferases and related reagents are used as reagents for diagnostics, quality control, environmental testing and other such analyses.

Preferred luciferases for use herein are the Aequorin protein, *Renilla* luciferase and *Cypridina* (also called *Vargula*) luciferase. Also, preferred are luciferases which react to produce red and/or near infrared light. These include luciferases found in species of *Aristostomias*, such as *A. scintillans, Pachystomias, Malacosteus*, such as *M. niger*.

The bioluminescent generating systems may also require additional components known to those of skill in the art. All bioluminescent reactions require molecular oxygen in the form of dissolved or bound oxygen. Thus, molecular oxygen, dissolved in water or in air or bound to a photoprotein, is the activator for bioluminescence reactions. Depending upon the form of the components, other activators include, but are not limited to, ATP (for firefly luciferase), flavin reductase for regenerating $FMNH_2$ from FMN (for bacterial systems), and $Ca^{++}$ or other suitable metal ions. While most of the systems provided herein will generate light when the luciferase and luciferin are mixed and exposed to air or water, the systems that use photoproteins that have bound oxygen, such as aequorin, will require exposure to $Ca^{++}$ or other suitable metal ion, which can be provided in the form of an aqueous composition of a calcium salt. In these instances, addition of a $Ca^{++}$ or other suitable metal ion to a mixture of aequorin luciferase and coelenterazine luciferin will result in generation of light. The *Renilla* system and other Anthozoa systems also require $Ca^{++}$ other suitable metal ion.

Ctenophores, such as *Mnemiopsis* (mnemiopsin) and *Beroe ovata* (berovin), and coelenterates, such as *Aequorea* (aequorin), *Obelia* (obelin) and *Pelagia*, produce bioluminescent light using similar chemistry. The Aequorin and *Renilla* systems are representative and are described in detail herein as exemplary and as among the presently preferred systems. The Aequorin and *Renilla* systems can use the same luciferin and produce light using the same chemistry, but each luciferase is different.

The Aequorin luciferase aequorin, as well as, for example, the luciferases mnemiopsin and berovin, is a photoprotein that includes bound oxygen and bound luciferin, requires $Ca^{++}$ (or other suitable metal ion) to trigger the reaction, and must be regenerated for repeated use. The *Renilla* luciferase also benefits from $Ca^{++}$ or other suitable metal ion but acts as a true enzyme because it is unchanged during the reaction and it requires dissolved molecular oxygen. See, e.g., Allen, D. G., J. R. Blinks, et al. (1977) "Aequorin luminescence: relation of light emission to calcium concentration—a calcium-independent component." *Science* 195(4282): 996-8; Blinks, J. R., F. G. Prendergast, et al. (1976) "Photoproteins as biological calcium indicators." *Pharmacological Reviews* 28(1): 1-93.; Charbonneau, H., K. A. Walsh, et al. (1985). "Amino acid sequence of the calcium-dependent photoprotein aequorin." *Biochemistry* 24(24): 6762-71; Cormier, M. J., D. C. Prasher, et al. (1989). "The enzymology and molecular biology of the $Ca^{2+-}$ activated photoprotein, aequorin." *Photochemistry & Photobiology* 49(4): 509-12.; Hannick, L. I., D. C. Prasher, et al. (1993). "Preparation and initial characterization of crystals Inouye, S. (2007). "Expression, purification and characterization of calcium-triggered luciferin-binding protein of *Renilla reniformis.*" *Protein Expression & Purification* 52(1): 66-73.; Inouye, S, and Y. Sahara (2008). "Identification of two catalytic domains in a luciferase secreted by the copepod *Gaussia princeps."* *Biochemical & Biophysical Research Communications* 365(1): 96-101; Inouye, S, and S. Sasaki (2006). "Blue fluorescent protein from the calcium-sensitive photoprotein aequorin: catalytic properties for the oxidation of coelenterazine as an oxygenase." *FEBS Letters* 580(8): 1977-82.; Inouye, S, and S. Sasaki (2007). "Imidazole-assisted catalysis of luminescence reaction in blue fluorescent protein from the photoprotein aequorin." *Biochemical & Biophysical Research Communications* 354(3): 650-5.; Inouye, S, and O, Shimomura (1997). "The use of *Renilla* luciferase, *Oplophorus* luciferase, and apoaequorin as bioluminescent reporter protein in the presence of coelenterazine analogues as substrate." *Biochemical & Biophysical Research Communications* 233(2): 349-53.; Inouye, S., K. Watanabe, et al. (2000). "Secretional luciferase of the luminous shrimp *Oplophorus gracilirostris*: cDNA cloning of a novel imidazopyrazinone luciferase(1)." *FEBS Letters* 481(1): 19-25.; Liu, Z. J., G. A. Stepanyuk, et al. (2006). "Crystal structure of obelin after $Ca^{2+-}$-triggered bioluminescence suggests neutral coelenteramide as the primary excited state." *Proceedings of the National Academy of Sciences of the United States of America* 103(8): 2570-5.; Loening, A. M., T. D. Fenn, et al. (2007). "Crystal structures of the luciferase and green fluorescent protein from *Renilla reniformis."* *Journal of Molecular Biology* 374(4): 1017-28.; Loening, A. M., T. D. Fenn, et al. (2006). "Consensus guided mutagenesis of *Renilla* luciferase yields enhanced stability and light output." *Protein Engineering, Design & Selection* 19(9): 391-400.; Loening, A. M., A. M. Wu, et al. (2007). "Red-shifted *Renilla reniformis* luciferase variants for imaging in living subjects. [see comment]." *Nature Methods* 4(8): 641-3.; Otto-Duessel, M., V. Khankaldyyan, et al. (2006). "In vivo testing of *Renilla* luciferase substrate analogs in an orthotopic murine model of human glioblastoma." *Molecular Imaging: Official Journal of the Society for Molecular Imaging* 5(2): 57-64.; Prasher, D. C., R. O. McCann, et al. (1987). "Sequence comparisons of complementary DNAs encoding aequorin isotypes." *Biochemistry* 26(5): 1326-32.18.; Ray, B. D., S. Ho, et al. (1985). "Proton NMR of aequorin. Structural changes concomitant with calcium-independent light emission." *Biochemistry* 24(16): 4280-7.; Shimomura, O. (1986). "Isolation and properties of various molecular forms of aequorin." *Biochemical Journal* 234(2): 271-7.; Shimomura, O. (1995). "Cause of spectral variation in the luminescence of semisynthetic aequorins." *Biochemical Journal* 306(Pt 2): 537-43.; Shimomura, O. (1995). "Luminescence of aequorin is triggered by the binding of two calcium ions." *Biochemical & Biophysical Research Communications* 211(2): 359-63.; Shimomura, O. (1995). "A short story of aequorin." *Biological Bulletin* 189(1): 1-5.; Shimomura, O. (1997). "Membrane permeability of coelenterazine analogues measured with fish eggs." *Biochemical Journal* 326(Pt 2): 297-8.; Shimomura, O. (2005). "The discovery of aequorin and green fluorescent protein." *Journal of Microscopy* 217(Pt 1): 1-15.; Shimomura, O., P. R. Flood, et al. (2001). "Isolation and properties of the luciferase stored in the ovary of the scyphozoan medusa *Periphylla periphylla."* *Biological Bulletin* 201 (3): 339-47.; Shimomura, O. and S. Inouye (1999). "The in situ regeneration and extraction of recombinant aequorin from *Escherichia coli* cells and the purification of extracted aequorin." *Protein Expression & Purification* 16(1): 91-5.; Shimomura, O. and F. H. Johnson (1969). "Properties of the bioluminescent protein aequorin." *Biochemistry* 8(10): 3991-7.; Shimomura, O. and F. H. Johnson (1970). "Mechanisms in the quantum yield of *Cypridina* bioluminescence." *Photochemistry & Photobiology* 12(4): 291-5.; Shimomura, O. and F. H. Johnson (1971). "Mechanism of the luminescent oxidation of *cypridina* luciferin." *Biochemical & Biophysical Research Communications* 44(2): 340-6.; Shimomura, O. and F. H. Johnson (1972). "Structure of the light-emitting moiety of aequorin." *Biochemistry* 11(9): 1602-8.; Shimomura, O. and F. H. Johnson (1973). "Further data on the specificity of aequorin luminescence to calcium." *Biochemical & Biophysical Research Communications* 53(2): 490-4.; Shimomura, O. and F. H. Johnson (1975). "Chemical nature of bioluminescence systems in coelenterates." *Proceedings of the National Academy of Sciences of the United States of America* 72(4): 1546-9.; Shimomura, O. and F. H. Johnson (1975). "Regeneration of the photoprotein aequorin." *Nature* 256(5514): 236-8.; Shimomura, O. and F. H. Johnson (1978). "Peroxidized coelenterazine, the active group in the photoprotein aequorin." *Proceedings of the National Academy of Sciences of the United States of America* 75(6): 2611-5.; Shimomura, O., F. H. Johnson, et al. (1974). "Mechanism of the luminescent intramolecular reaction of aequorin." *Biochemistry* 13(16): 3278-86.; Shimomura, O., F. H. Johnson, et al. (1961). "Purification and properties of *Cypridina* luciferase." *Journal of Cellular & Comparative Physiology* 58: 113-23.; Shimomura, O., Y. Kishi, et al. (1993). "The relative rate of aequorin regeneration from apoaequorin and coelenterazine analogues." *Biochemical Journal* 296(Pt 3): 549-51.; Shimomura, O., T. Masugi, et al. (1978). "Properties and reaction mechanism of the bioluminescence system of the deep-sea shrimp *Oplophorus grachlorostris.*" *Biochemistry* 17(6): 994-8.; Shimomura, O., B. Musicki, et al. (1989). "Semi-synthetic aequorins with improved sensitivity to Ca2+ ions." *Biochemical Journal* 261(3): 913-20.; Shimomura, O., B. Musicki, et al. (1993). "Light-emitting properties of recombinant semi-synthetic aequorins and recombinant fluorescein-conjugated aequorin for measuring cellular calcium." *Cell Calcium* 14(5): 373-8.; Shimomura, O. and A. Shimomura (1981). "Resistivity to denaturation of the apoprotein of aequorin and reconstitution of the luminescent photoprotein from the partially denatured apoprotein." *Biochemical Journal* 199(3): 825-8.; Shimomura, O. and K. Teranishi (2000). "Light-emitters involved in the luminescence of coelenterazine." *Luminescence* 15(1): 51-8.; Shimomura, O., C. Wu, et al. (1998). "Evaluation of five imidazopyrazinone-type chemiluminescent superoxide probes and their application to the measurement of superoxide anion generated by *Listeria monocytogenes.*" *Analytical Biochemistry* 258(2): 230-5.

This system is among the preferred systems for use herein. As will be evident, since the aequorin photoprotein includes noncovalently bound luciferin and molecular oxygen, it is suitable for storage in this form as a lyophilized powder or encapsulated into a selected delivery vehicle. The system can be encapsulated into pellets, such as liposomes or other delivery vehicles. When used, the vehicles are contacted with a composition, even tap water, that contains $Ca^{++}$ or other suitable metal ion, to produce a mixture that glows.

It is also understood that these mixtures will also contain any additional salts or buffers or ions that are necessary for each reaction to proceed. Since these reactions are well-characterized, those of skill in the art will be able to determine precise proportions and requisite components. Selection of components will depend upon the apparatus, article of manufacture and luciferase. Factors for consideration in selecting a bioluminescent-generating system, include, but are not limited to: the targeting agent used in combination with the bioluminescence; the medium in which the reaction is run; stability of the components, such as temperature or pH sensitivity; shelf life of the components; sustainability of the light emission, whether constant or intermittent; availability of components; desired light intensity; color of the light; and other such factors.

D. Methods of Use

In all embodiments, all but one component, either the luciferase or luciferin, of a bioluminescence generating system will be mixed or packaged together or otherwise combined. The mixture and the remaining component will be separately delivered to a tissue area of interest to activate bioluminescence in the subject.

In one preferred embodiment for use in surgical procedures, a targeting agent conjugate includes a targeting agent that binds to targeted tissue coupled to either the mixture or the remaining component. The other composition (the remaining component or the mixture) is then administered to the tissue, causing initiation of bioluminescence. For example, the targeting agent conjugate can administered via injection or other suitable route that causes the targeting agent conjugate to bind to targeted tissue by interaction with a tissue-specific cell surface protein. During surgery the tissue is contacted, with the other composition, typically by spraying the area or local injection, and any tissue to which conjugate is bound will glow. This embodiment is typical but not limited to the sentinel lymph node application described herein.

However, surface binding to target tissue is not a mandatory step or method of the invention. The bioluminescent generating system components may be mixed immediately prior to infusion, or may be mixed during infusion by the use of a simple Y tube, where one arm delivers the enzyme and one arm delivers substrate, or may be activated by sequential administration where one of the components, luciferin or luciferase, is delivered first, follow by subsequent delivery of the other component to achieve bioluminescence.

The glow should be sufficient to see under dim visible light or, if necessary, in the dark. This is typical but not limited to the bioluminescent cholangiography and bowel anastomotic patency testing methods described herein, whereby the duct or hollow viscus is accessed with an angio-catheter or similar catheter or cannula which is connected to a short length of a Y-tubing which is used to infuse the bioluminescence generating system (or luciferin and luciferase). Surgical viewing may be by naked eye or endoscopic methods as described. For navigational or diagnostic mapping applications intra-operative administration of the bioluminescent agent is via any suitable route, whereby the agent fills and illuminates the tubes, ducts, lumens, chambers, vessels or hollow organs.

In general, since the result to be achieved is the production of light visible to the naked eye for qualitative, not quantitative, diagnostic purposes, the precise proportions and amounts of components of the bioluminescence reaction need not be stringently determined or met. They must be sufficient to produce light. Generally, an amount of luciferin and luciferase sufficient to generate a visible glow is used; this amount can be readily determined empirically and is dependent upon the selected system and selected application. Where quantitative measurements are required, more precision may be required.

Higher concentrations may be used if the glow is not sufficiently bright. Alternatively, a microcarrier coupled to more than one luciferase molecule linked to a targeting agent may be utilized to increase signal output. Also because the conditions in which the reactions are used are not laboratory conditions, and the components are subject to storage, higher concentration may be used to overcome any loss of activity.

E. Reaction Mixture Formulations

Luciferase for use in accordance with the invention will be provided at a concentration of between about 0.01 mg and 100 mg per liter of reaction mixture (the total of all components of the bioluminescence mixture). In embodiments in which the luciferase acts catalytically and does not need to be regenerated, lower amounts of luciferase can be used. In those in which it is changed during the reaction, it also can be replenished; typically higher concentrations will be selected. In most typical applications, the luciferase will be provided at a concentration of 0.1 to 20 mg, preferably 0.1 to 10 mg, more preferably between about 1 and 10 mg per liter of reaction mixture. Concentrations of at least 1 mg or more are preferred for a brighter result.

Luciferin will be provided at a concentration of between about 0.01 mg and 100 mg per liter of reaction mixture, and In most typical applications, the luciferin will be provided at a concentration of 0.1 to 20 mg, preferably 0.1 to 10 mg, more preferably between about 1 and 10 mg per liter of reaction mixture. Concentrations of at least 1 mg or more are preferred. Additional luciferin can be added to many of the reactions to continue the reaction. When preparing coated substrates, coating compositions containing higher concentrations of the luciferase or luciferin may be used.

The reaction mixture will contain additional ingredients as needed to enhance viscosity, adhesion, or to activate the bioluminescent reaction may be included in amounts from about 0.01 mg/l, to about 10 mg/l or more of the reaction mixture. This can include but is not limited to polyethylene glycols of molecular weights from 400 to 20,000; water-soluble cellulose esters such as methylcellulose, ethylcellulose, carboxyethyl cellulose, carboxymethyl celluose; bacterially-derived carbohydrates such as dextran and beta-cyclodextrin, as well as chemically-modified cyclodextrins well known to those skilled in the art; chemically-modified starches; albumin proteins including ovalbumin, human serum albumin, bovine serum albumin, canine serum albumin, and feline serum albumin; simple alcohols such as glycerol, 1,3-propanediol, and ethanol; carbohydrate alcohols such as sorbitol, mannitol, pentaerythreitol, and water soluble esters thereof; non-reducing sugars, biologically-compatible fluorinated compounds which increase oxygen transport, including but not limited to perfluorotributylamine, perfluorodecalin, and perfluoroalcohols and their esters; solubilizers and nonionic and zwiterionic detergents including but not limited to the Tween, Pluronic, Triton series and cholic acid, sodium desoxycholate, CHAPS (Cholamidopropanesulfonate), biologically compatible organic buffers typified by but not limited to TRIS, BIS-TRIS, HEPES, MES, and inorganic ions typified by but not limited to Calcium ion ($Ca^{++}$).

Thus, for example, 5 mg of luciferin, such as coelenterazine, in one liter of water will glow brightly for at least about 10 to 20 minutes, depending on the temperature of the water, when about 10 mgs of luciferase, such as aequorin photoprotein luciferase or luciferase from *Renilla*, is added thereto in presence of $Ca^{++}$. Increasing the concentration of luciferase, for example, to 100 mg/L, provides a particularly brilliant light display.

It is understood, that concentrations and amounts to be used depend upon the selected bioluminescence generating system but these may be readily determined empirically. Proportions, particularly those used when commencing an empirical determination, are generally those used for analytical purposes, and amounts or concentrations are at least those used for analytical purposes, but the amounts can be increased, particularly if a sustained and brighter glow is desired.

F. Aequorin Systems

The bioluminescence photoprotein aequorin is isolated from a number of species of the jellyfish *Aequorea*. It is a 22 kilodalton [kDa] molecular weight peptide complex. The native protein contains oxygen and a heterocyclic compound coelenterazine, a luciferin, noncovalently bound thereto. The protein contains three calcium binding sites. Upon addition of trace amounts $Ca^{++}$ or other suitable metal ion, such as strontium to the photoprotein, it undergoes a conformational change that catalyzes the oxidation of the bound coelenterazine using the protein-bound oxygen. Luminescence is triggered by calcium, which releases oxygen and the luciferin substrate producing apoaequorin. Energy from this oxidation is released as a flash of blue light, centered at 469 nm. Concentrations of calcium ions as low as $10^{-6}$ M are sufficient to trigger the oxidation reaction. Aequorin does not require dissolved oxygen.

Figure 2:
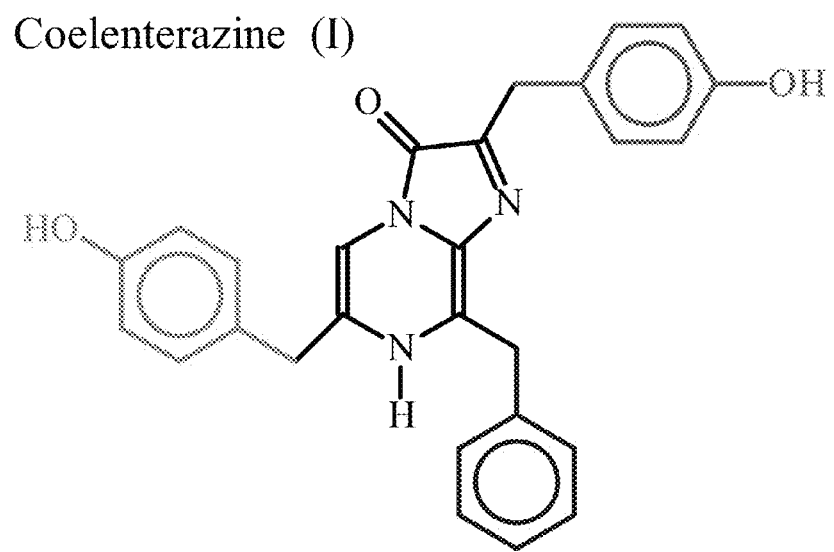
FIG. 2 is an illustration of the chemical structure of coelenterazine (Structure I).

The aequorin luciferin coelenterazine is a molecule having Structure I shown in FIG. 2, and analogs and sulfated derivatives thereof.

Figure 3:
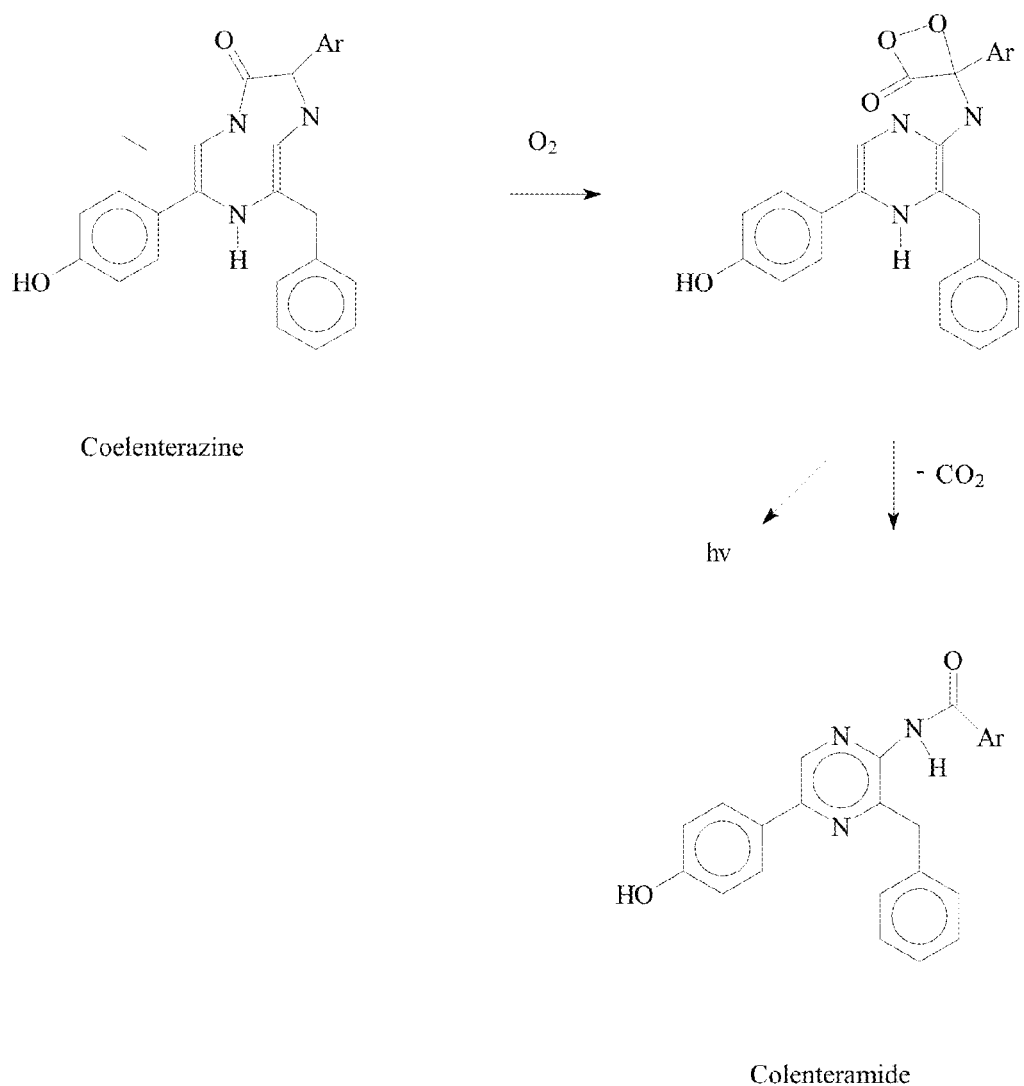
FIG. 3 is an illustration of the changes in the chemical structure of coelenterazine during bioluminescence.

The reaction of coelenterazine when bound to the aequorin photoprotein with bound oxygen and in the presence of $Ca^{++}$ is shown in FIG. 3.

Naturally-occurring apoaequorin is not a single compound but rather is a mixture of microheterogeneous molecular species. Aequoria jellyfish extracts contain as many as twelve distinct variants of the protein. DNA encoding numerous forms has been isolated.

Numerous isoforms of the aequorin apoprotein been isolated. DNA encoding these proteins has been cloned, and the proteins and modified forms thereof have been produced using suitable host cells. DNA encoding apoaequorin or variants thereof is useful for recombinant production of high quantities of the apoprotein. The preferred aequorin is produced using DNA, and known to those of skill in the art or modified forms thereof. The DNA encoding aequorin is expressed in a host cell, such as *E. coli*, isolated and reconstituted to produce the photoprotein. Of interest herein are forms of the apoprotein that have been modified so that the bioluminescent activity is greater than unmodified apoaequorin.

The photoprotein can be reconstituted by combining the apoprotein, such as a protein recombinantly produced in *E. coli*, with the luciferin, coelenterazine (preferably a sulfated derivative thereof, or an analog thereof), such as a synthetic coelenterazine, in the presence of molecular oxygen and a reducing agent such as 2-mercaptoethanol, and also EDTA or EGTA to tie up any $Ca^{++}$ to prevent triggering the oxidation reaction until desired. (DNA encoding a modified form of the apoprotein that does not require 2-mercaptoethanol for reconstitution is also possible). The constituents of the bioluminescence generating reaction can be mixed under appropriate conditions to regenerate the photoprotein and concomitantly have the photoprotein produce light.

For use in certain embodiments herein, the apoprotein and other components of the aequorin bioluminescence generating system are packaged or provided as a mixture, which, when desired, is subjected to conditions under which the photoprotein reconstitutes from the apoprotein, luciferin and oxygen. Particularly preferred are forms of the apoprotein that do not require a reducing agent, such as 2-mercaptoethanol, for reconstitution. The photoproteins and luciferases from related species, such as *Obelia* are also contemplated for use herein. DNA encoding the Calcium-activated photoprotein obelin from the hydroid polyp *Obelia longissima* is known and available [see, e.g., Deng, L., S. V. Markova, et al. (2004). "Preparation and X-ray crystallographic analysis of the $Ca^{2+-}$-discharged photoprotein obelin." *Acta Crystallographica Section D-Biological Crystallography* 60(Pt 3): 512-4.]. In general for use herein, the components of the bioluminescence are packaged or provided so that there is insufficient metal ions to trigger the reaction. When used, the trace amounts of triggering metal ion, particularly $Ca^{++}$ is contacted with the other components. For a more sustained glow, aequorin can be continuously reconstituted or can be added or can be provided in high excess.

The light reaction is triggered by adding $Ca^{++}$ at a concentration sufficient to overcome the effects of the chelator and achieve the $10^{-6}$ M concentration. Because such low concentrations of $Ca^{++}$ can trigger the reaction, for use in the methods herein, higher concentrations of chelator may be included in the compositions of photoprotein. Accordingly, higher concentrations of added $Ca^{++}$ in the form of a calcium salt will be required. Precise amounts may be empirically determined. For use herein, it may be sufficient to merely add water to the photoprotein, which is provided in the form of a concentrated composition or in lyophilized or powdered form. Thus, for purposes herein, addition of small quantities of $Ca^{++}$, such as those present in phosphate buffered saline (PBS) or other suitable buffers or the moisture on the tissue to which the compositions are contacted, should trigger the bioluminescence reaction.

The photoprotein aequorin, which contains apoaequorin bound to a coelenterate luciferin molecule, and *Renilla* luciferase, can use the same coelenterate luciferin. The aequorin photoprotein catalyses the oxidation of coelenterate luciferin [coelenterazine] to oxyluciferin [coelenteramide] with the concomitant production of blue light [lambda max=469 nm]. (See FIG. 3).

The sulfate derivative of the coelenterate luciferin [lauryl-luciferin] is particularly stable in water, and thus may be used in a coelenterate-like bioluminescent system. In this system, adenosine diphosphate (ADP) and a sulphakinase are used to convert the coelenterazine to the sulphated form. Sulfatase is then used to reconvert the lauryl-luciferin to the native coelenterazine. Thus, the more stable lauryl-luciferin is used in the item to be illuminated and the luciferase combined with the sulfatase are added to the luciferin mixture when illumination is desired.

The bioluminescent system of *Aequorea* is particularly suitable for use in the methods herein. The particular amounts and the manner in which the components are provided depend upon the type of neoplasia or specialty tissue to be visualized. This system can be provided in lyophilized form, which will glow upon addition of $Ca^{++}$. It can be encapsulated, linked to microcarriers, such as microbeads, or in as a compositions, such as a solution or suspension, preferably in the presence of sufficient chelating agent to prevent triggering the reaction. The concentration of the aequorin photoprotein will vary and can be determined empirically. Typically concentrations of at least 0.1 mg/l, more preferably at least 1 mg/l and higher, will be selected. In certain embodiments, 1-10 mg luciferin/100 mg of luciferase will be used.

G. *Renilla* Systems

The *Renilla* system is representative of coelenterate bioluminesence systems. *Renilla*, also known as sea pansies, are members of the class of coelenterates Anthozoa, which includes other bioluminescent genera, such as *Cavarnularia, Ptilosarcus, Stylatula, Acanthoptilum*, and *Parazoanthus*. Bioluminescent members of the Anthozoa genera contain luciferases and luciferins that are similar in structure [see, e.g., Cormier et al. (1973) J. Cell. Physiol. 81:291-298; see, also Ward et al. (1975) Proc. Natl. Acad. Sci. U.S.A. 72:2530-2534]. The luciferases and luciferins from each of these anthozoans crossreact with one another and produce a characteristic blue luminescence.

*Renilla* luciferase and the other coelenterate and ctenophore luciferases, such as the aequorin photoprotein, use imidazopyrazine substrates, particularly the substrates generically called coelenterazine [see, Formula I (FIG. 2) above]. Other genera that have luciferases that use a coelenterazine include: squid, such as *Chiroteuthis, Eucleoteuthis, Onychoteuthis, Watasenia*, cuttlefish, *Sepiolina*; shrimp, such as *Oplophorus, Acanthophyra, Sergestes*, and *Gnathophausia*; deep-sea fish, such as *Argyropelecus, Yarella, Diaphus, Gonadostomias* and *Neoscopelus*. *Renilla* luciferase does not, however, have bound oxygen, and thus requires dissolved oxygen in order to produce light in the presence of a suitable luciferin substrate. Since *Renilla* luciferase acts as a true enzyme, i.e., it does not have to be reconstituted for further use, the resulting luminescence can be long-lasting in the presence of saturating levels of luciferin. Also, *Renilla* luciferase is relatively stable to heat. *Renilla* luciferase, DNA encoding *Renilla* luciferase, and use of the DNA to produce recombinant luciferase, as well as DNA encoding luciferase from other coelenterates, are well known. (See for example Bhaumik, S., X. Z. Lewis, et al. (2004). "Optical imaging of *Renilla* luciferase, synthetic *Renilla* luciferase, and firefly luciferase reporter gene expression in living mice." *Journal of Biomedical Optics* 9(3): 578-86.; Inouye, S, and O, Shimomura (1997). "The use of *Renilla* luciferase, *Oplophorus* luciferase, and apoaequorin as bioluminescent reporter protein in the presence of coelenterazine analogues as substrate." *Biochemical & Biophysical Research Communications* 233(2): 349-53.; Loening, A. M., T. D. Fenn, et al. (2007). "Crystal structures of the luciferase and green fluorescent protein from *Renilla reniformis*." *Journal of Molecular Biology* 374(4): 1017-28. Loening, A. M., T. D. Fenn, et al. (2006). "Consensus guided mutagenesis of *Renilla* luciferase yields enhanced stability and light output." *Protein Engineering, Design & Selection* 19(9): 391-400.; Loening, A. M., A. M. Wu, et al. (2007). "Red-shifted *Renilla reniformis* luciferase variants for imaging in living subjects." *Nature Methods* 4(8): 641-3.)

The DNA encoding *Renilla* luciferase and host cells containing such DNA provide a convenient means for producing large quantities of the enzyme. When used herein, the *Renilla* luciferase can be packaged in lyophilized form, encapsulated in a vehicle, either by itself or in combination with the luciferin substrate. Prior to use the mixture is contacted with an aqueous composition, preferably a phosphate buffered saline pH 7-8; dissolved $O_2$ will activate the reaction. Final concentrations of luciferase in the glowing mixture will be on the order of 0.01 to 1 mg/l or more. Concentrations of luciferin will be at least about $10^{-8}$ M, but preferably are 1 to 100 or more orders of magnitude higher to produce a long lasting bioluminescence.

In certain embodiments herein, about 1 to 10 mg, or preferably 2-5 mg, more preferably about 3 mg of coelenterazine will be used with about 100 mg of *Renilla* luciferase. The precise amounts, of course can be determined empirically, and, also will depend to some extent on the ultimate concentration and application. In one example, the addition of about 0.25 ml of a crude extract from the bacteria that express *Renilla* to 100 ml of a suitable assay buffer and about 0.005 mg of coelenterazine was sufficient to produce a visible and lasting glow Lyophilized mixtures, and compositions containing the *Renilla* luciferase are also provided. The luciferase or mixtures of the luciferase and luciferin may also be encapsulated into a suitable delivery vehicle, such as a liposome, glass particle, capillary tube, drug delivery vehicle, gelatin, time release coating or other such vehicle. The luciferase may also be linked to a substrate, such as biocompatible materials.

G. Crustacean, Particularly *Cyrpidina* Systems

The ostracods, such as *Vargula serratta, V. hilgendorfii* and *V. noctiluca* are small marine crustaceans, sometimes called sea fireflies. These sea fireflies are found in the waters off the coast of Japan and emit light by squirting luciferin and luciferase into the water, where the reaction, which produces a bright blue luminous cloud, occurs. The reaction involves only luciferin, luciferase and molecular oxygen, and, thus, is very suitable for application herein.

The systems, such as the *Vargula* bioluminescent systems, are particularly preferred herein because the components are stable at room temperature if dried and powdered and will continue to react even if contaminated. Further, the bioluminescent reaction requires only the luciferin/luciferase components in concentrations as low as 1:40 parts per billion to 1:100 parts per billion, water and molecular oxygen to proceed. Importantly an exhausted system can renew by addition of luciferin.

*Vargula* luciferase is water soluble and is among those preferred for use in the methods herein. *Vargula* luciferase is a 555-amino acid polypeptide that has been produced by isolation from *Vargula* and also using recombinant technology by expressing the DNA in suitable bacterial and mammalian hosts.

Methods for purification of *Vargula* [also known as *Cypridina*] luciferase are well known. For example, crude extracts containing the active can be readily prepared by homogenizing or crushing the *Vargula* shrimp. In other embodiments, a preparation of *Cypridina hilgendorfii* luciferase can be prepared by immersing stored frozen *C. hilgendorfii* in distilled water containing, 0.5-5.0 M salt, preferably 0.5-2.0 M sodium or potassium chloride, ammonium sulfate, at 0-30° C., preferably 0-10° C., for 1-48 hr, preferably 10-24 hr, for extraction followed by hydrophobic chromatography and then ion exchange or affinity chromatography.

The luciferin can be isolated from ground freeze-dried *Vargula* by heating the extract, which destroys the luciferase but leaves the luciferin intact

*Vargula* [also known as *Cypridina*] luciferase is preferably produced by expression of cloned DNA encoding the luciferase. DNA encoding the luciferase or variants thereof is introduced into *E. coli* using appropriate vectors and isolated using standard methods.

Natural *Vargula* [also known as *Cypridina*] luciferase has a substituted imidazopyrazine nucleus. Analogs thereof well known in the prior art and other compounds that react with the luciferin in a light producing reaction also may be used. Other bioluminescent organisms that have luciferases that can react with the *Vargula* luciferin include, the genera *Apogon, Parapriacanthus* and *Porichthys*.

The luciferin upon reaction with oxygen forms a dioxetanone intermediate [which includes a cyclic peroxide similar to the firefly cyclic peroxide molecule intermediate]. In the final step of the bioluminescent reaction, the peroxide breaks down to form $CO_2$ and a molecule with the C=O bond in an electronically excited state. The excited state molecule then returns to the ground state and in this process emits a blue to blue-green light.

The optimum pH for the reaction is about 7. For purposes herein, any pH at which the reaction occurs may be used. The concentrations of reagents are those normally used for analytical reactions or higher [see, e.g., Thompson et al. (1990) Gene 96:257-262]. Typically concentrations of the luciferase between 0.1 and 10 mg/l, preferably 0.5 to 2.5 mg/l will be used. Similar concentrations or higher concentrations of the luciferin may be used.

H. Other Fluorescent Protein Systems

Blue light is produced using the *Renilla* luciferase or the *Aequorea* photoprotein in the presence of $Ca^{++}$ and the coelenterazine luciferin or analog thereof. By means of Dexter-Forster energy transfer, this light can be converted into a light of a different and longer wavelength if a green fluorescent protein (GFP) is added to the reaction. Green fluorescent proteins, which have been purified and also are used by cnidarians as energy-transfer acceptors. GFPs fluoresce in vivo upon receiving energy from a luciferase-oxyluciferein excited-state complex or a $Ca^{++}$-activated photoprotein. This process is known as Bioluminescent Resonant Energy Transfer (BRET) and has been utilized extensively for a wide variety of biological assay systems. In GFP, the chromophore is series of adjacent modified amino acid residues within the polypeptide. The best characterized GFPs are those of *Aequorea* and *Renilla*. For example, a green fluorescent protein from *Aequorea Victoria* contains 238 amino acids, absorbs blue light and emits green light. Thus, inclusion of this protein in a composition containing the aequorin photoprotein charged with coelenterazine and oxygen, can, in the presence of calcium, result in the production of green light. Thus, it is contemplated that GFPs may be included in the bioluminescence generating reactions that employ the aequorin or *Renilla* luciferases or other suitable luciferase in order to enhance or alter color of the resulting bioluminescence. Many genetically-altered GFPs are well known in the prior art, and these can produce colors from the blue to the red.

GFPs are activated by blue light to emit green light and thus may be used in the absence of luciferase and in conjunction with an external light source to illuminate neoplasia and specialty tissues, as described herein. Similarly, blue fluorescent proteins (BFPs), such as from *Vibrio fischeri, Vibrio harveyi* or *Photobacterium phosphoreum*, may be used in conjunction with an external light source of appropriate wavelength to generate blue light. In particular, GFPs, and/or BFPs or other such fluorescent proteins may be used in the methods described herein using a targeting agent conjugate by illuminating the conjugate with light of an appropriate wavelength to cause the fluorescent proteins to fluoresce.

Such systems are particularly of interest because no luciferase is needed to activate the photoprotein. These fluorescent proteins may also be used in addition to bioluminescence generating systems to enhance or create an array of different colors.

I. Phycobiliprotein Systems

Phycobiliproteins are water soluble fluorescent proteins derived from cyanobacteria. These proteins have been used as fluorescent labels in immunoassays; the proteins have been isolated and DNA encoding them is also available; the proteins are commercially available from, for example, ProZyme, Inc., San Leandro, Calif.

In these organisms, the Phycobiliproteins are arranged in subcellular structures termed phycobilisomes, and function as accessory pigments that participate in photosynthetic reactions by absorbing visible light and transferring the derived energy to chlorophyll via a direct fluorescence energy transfer mechanism.

Two classes of phycobiliproteins are known based on their color: phycoerythrins (red) and phycocyanins (blue), which have reported absorption maximal between 490 and 570 nm and between 610 and 665 nm, respectively. Phycoerythrins and phycocyanins are heterogeneous complexes composed of different ratios of alpha and beta monomers to which one or more class of linear tetrapyrrole chromophores are covalently bound. Particular phycobiliproteins may also contain a third subunit which often associated with aggregate proteins.

All phycobiliproteins contain either phycothrombilin or phycoerythobilin chromophores, and may also contain other bilins phycourobilin, cryptoviolin or the 697 nm bilin. The subunit is covalently bound with phycourobilin which results in the 495-500 nm absorption peak of B- and R-phycoerythrins. Thus, the spectral characteristics of phycobiliproteins may be influenced by the combination of the different chromophores, the subunit composition of the apophycobiliproteins and/or the local environment effecting the tertiary and quaternary structure of the phycobiliproteins.

As described above for GFPs and BFPs, phycobiliproteins are also activated by visible light of the appropriate wavelength and, thus, may be used in the absence of luciferase and in conjunction with an external light source to illuminate neoplasia and specialty tissues, as described herein. These proteins may be used in combination with other fluorescent proteins and/or bioluminescence generating systems to produce an array of colors or to provide different colors over time. Attachment of phycobiliproteins to solid support matrices is known. Therefore, phycobiliproteins may be coupled to microcarriers coupled to one or more components of the bioluminescent reaction, preferably a luciferase, to convert the wavelength of the light generated from the bioluminescent reaction. Microcarriers coupled to one or more phycobiliproteins may be used in any of the methods provided herein.

The conversion of blue or green light to light of a longer wavelength, i.e., red or near infra-red, is particularly preferred for the visualization of deep neoplasias or specialty tissues using a laparoscope or computer tomogram imaging system. Thus, when a change in the frequency of emitted light is desired, the phycobiliprotein, or other spectral shifter, such as synthetic fluorochrome, green fluorescent proteins, red fluorescent proteins, and substrates altered chemically or enzymatically to cause shifts in frequency of emission can be included with the bioluminescent generating components.

J. Membrane Permeant Analogs of Coelenterazine

The present invention may not be limited to the above embodiments, but may use various bioluminescent substances other than shown in the embodiments.

Figure 4:
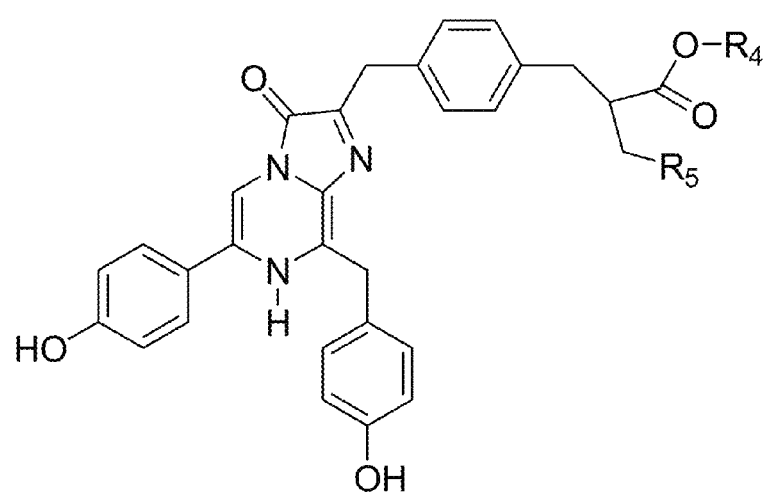
FIG. 4 is an illustration of the chemical structure of a membrane permeant analog of coelenterazine (Structure II).

This invention specifically includes compositions which are membrane permeant analogs of coelenterazine, the substrate for *renilla* luciferase, having the following Structure II:

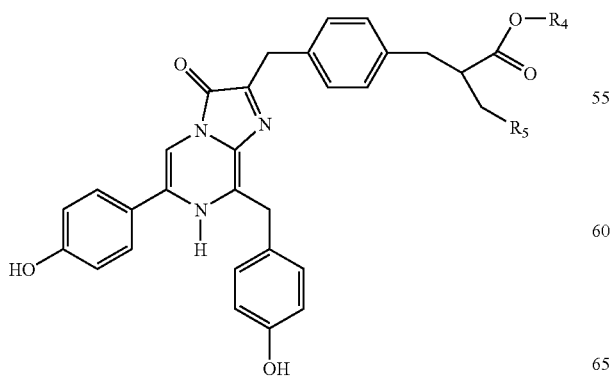

wherein R4 and R5 may independently be alkyl or aralkyl, and R4 may be aryl or optionally substituted aryl, aralkyl or optionally substituted aralkyl, and R5 may be alkyl, optionally substituted alkyl, alkoxy, aralkyl, or optionally substituted aralkyl, aryl, or a heterocycle. Structure II is also shown in FIG. 4.

Figure 5:
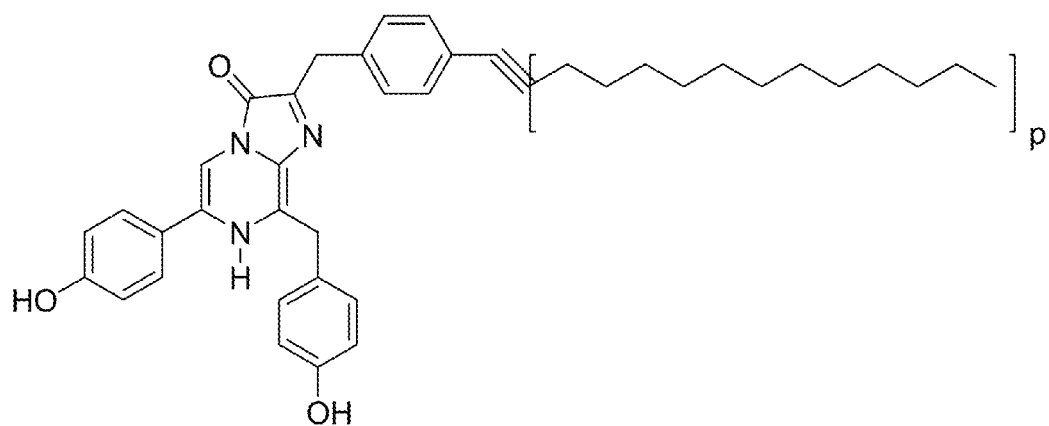
FIG. 5 is an illustration of the chemical structure of a membrane permeant analog of coelenterazine (Structure III).

The present invention further includes the related class of membrane permeant coelenterazine analogs which are exemplified by the following Structure III:

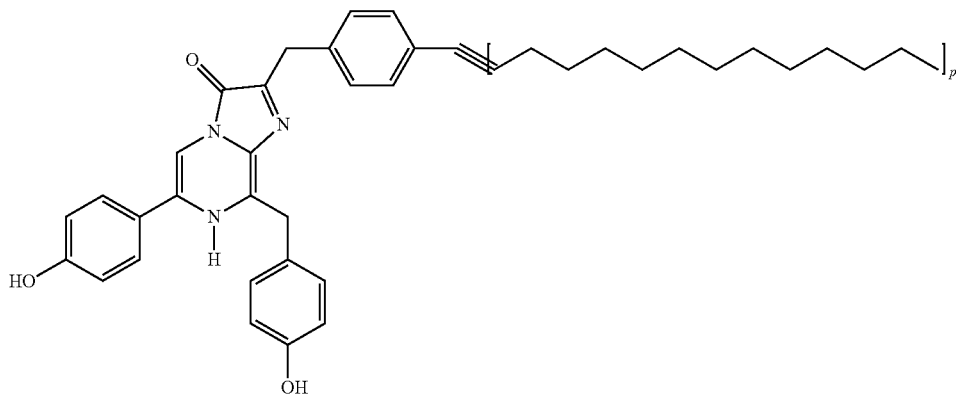

wherein p may be an integer ranging from 1 to 20. Structure III is also shown in FIG. 5.

Figure 6:
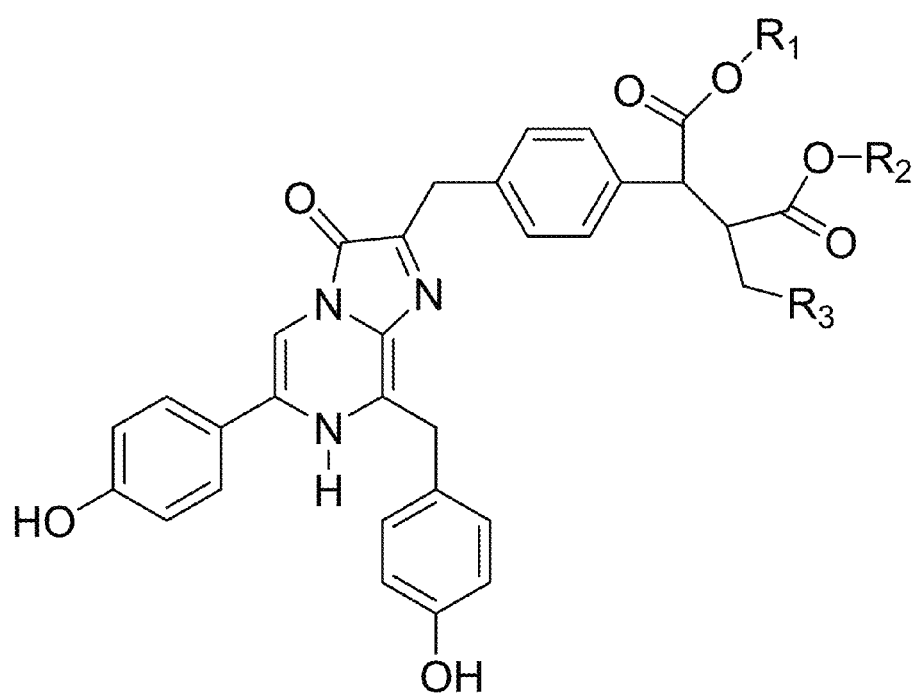
FIG. 6 is an illustration of the chemical structure of a membrane permeant analog of coelenterazine (Structure IV).
Figure 7:
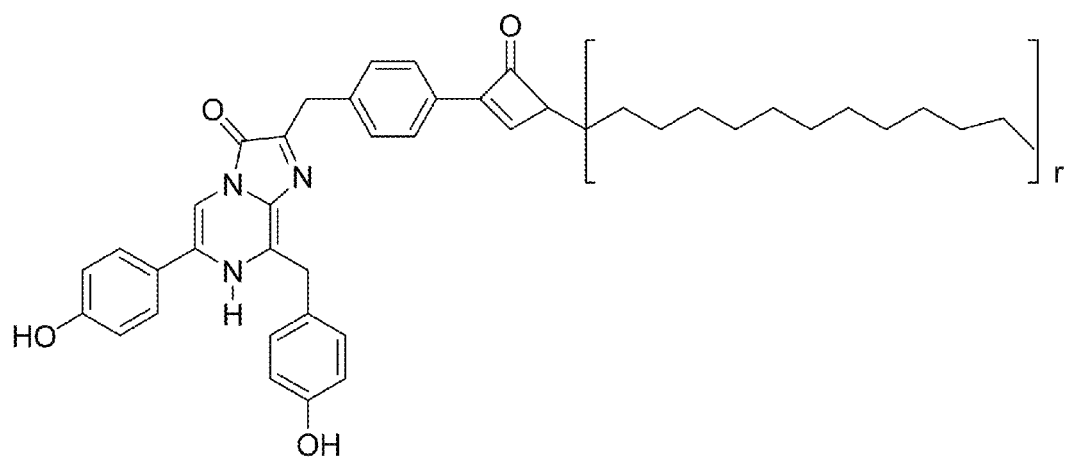
FIG. 7 is an illustration of the chemical structure of a membrane permeant analog of coelenterazine (Structure V).

The present invention further includes the related class of membrane permeant coelenterazine analogs which are exemplified by the following Structure IV:

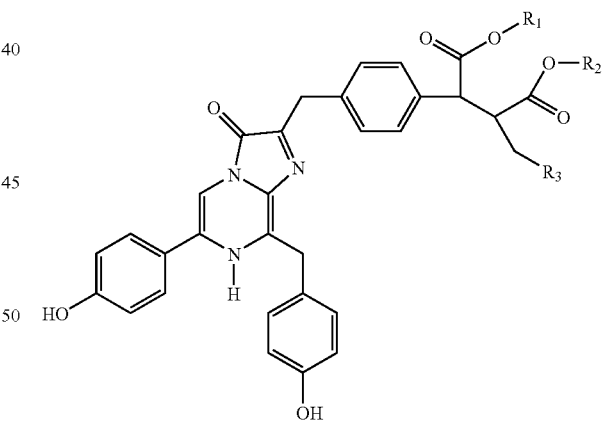

wherein R1, R2, and R3 are independently alkyl, optionally substituted alkyl, alkenyl, or aralkyl. Structure IV is also shown in FIG. 6:

The present invention further includes the related class of membrane permeant coelenterazine analogs which are exemplified by the following Structure V:

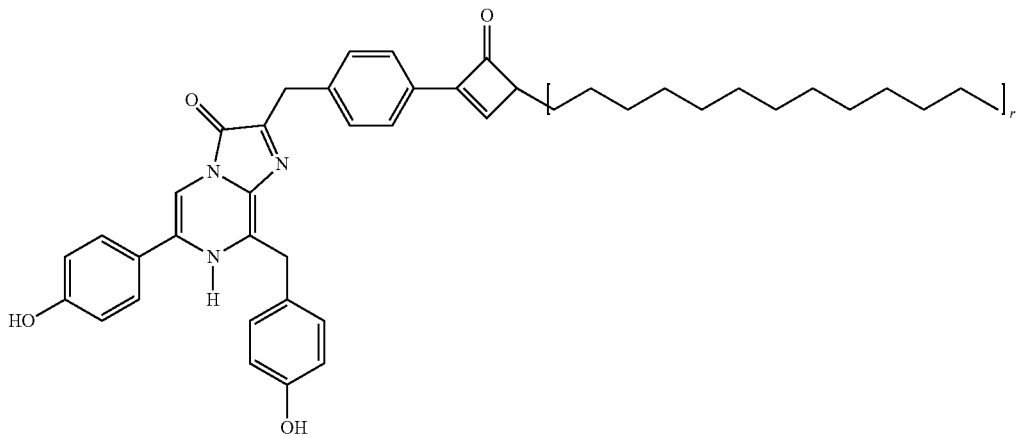

in which r may be an integer from 1 to 20. Structure V is also shown in FIG. 7.

Figure 8:
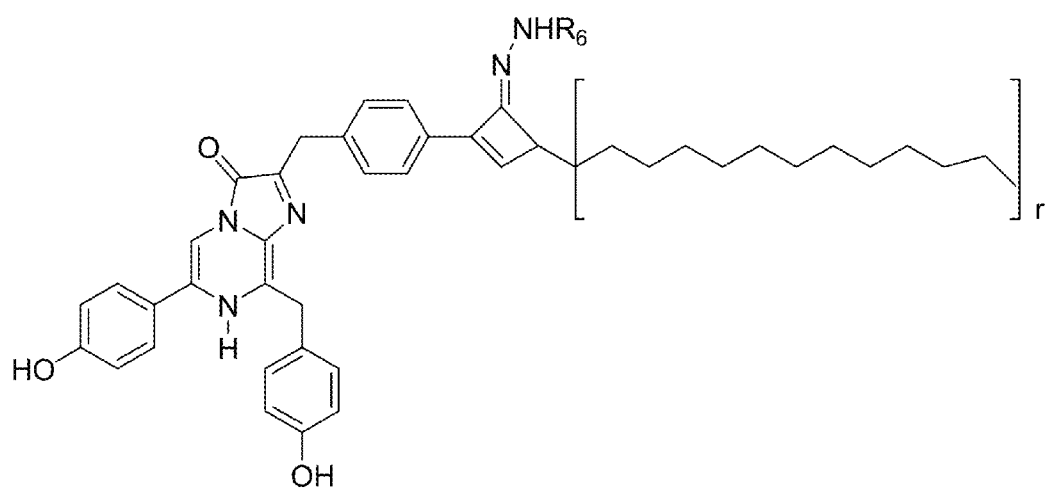
FIG. 8 is an illustration of the chemical structure of a membrane permeant analog of coelenterazine (Structure VI).

The present invention further includes the related class of membrane permeant coelenterazine analogs which are exemplified by the following by the following Structure VI:

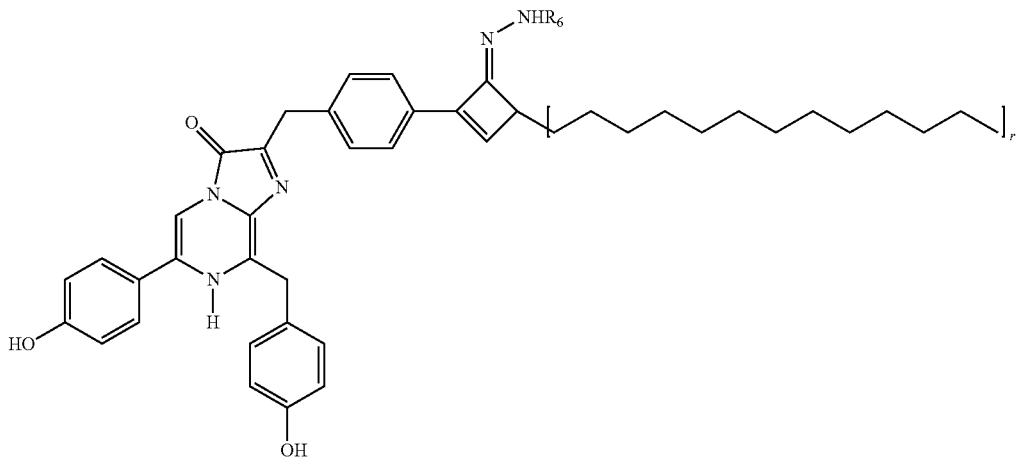

in which r may be an integer from 1 to 20 and R6 may be alkyl, aryl, aralkyl, optionally substituted alkyl, optionally substituted aryl, optionally substituted aralkyl, or alkoxyalkyl. Structure VI is also shown in FIG. 8.

The steps of the general synthetic schema for preparation of the above identified membrane permeant analogs of coelenterazine is shown in FIGS. 36-39.

Figure 9:
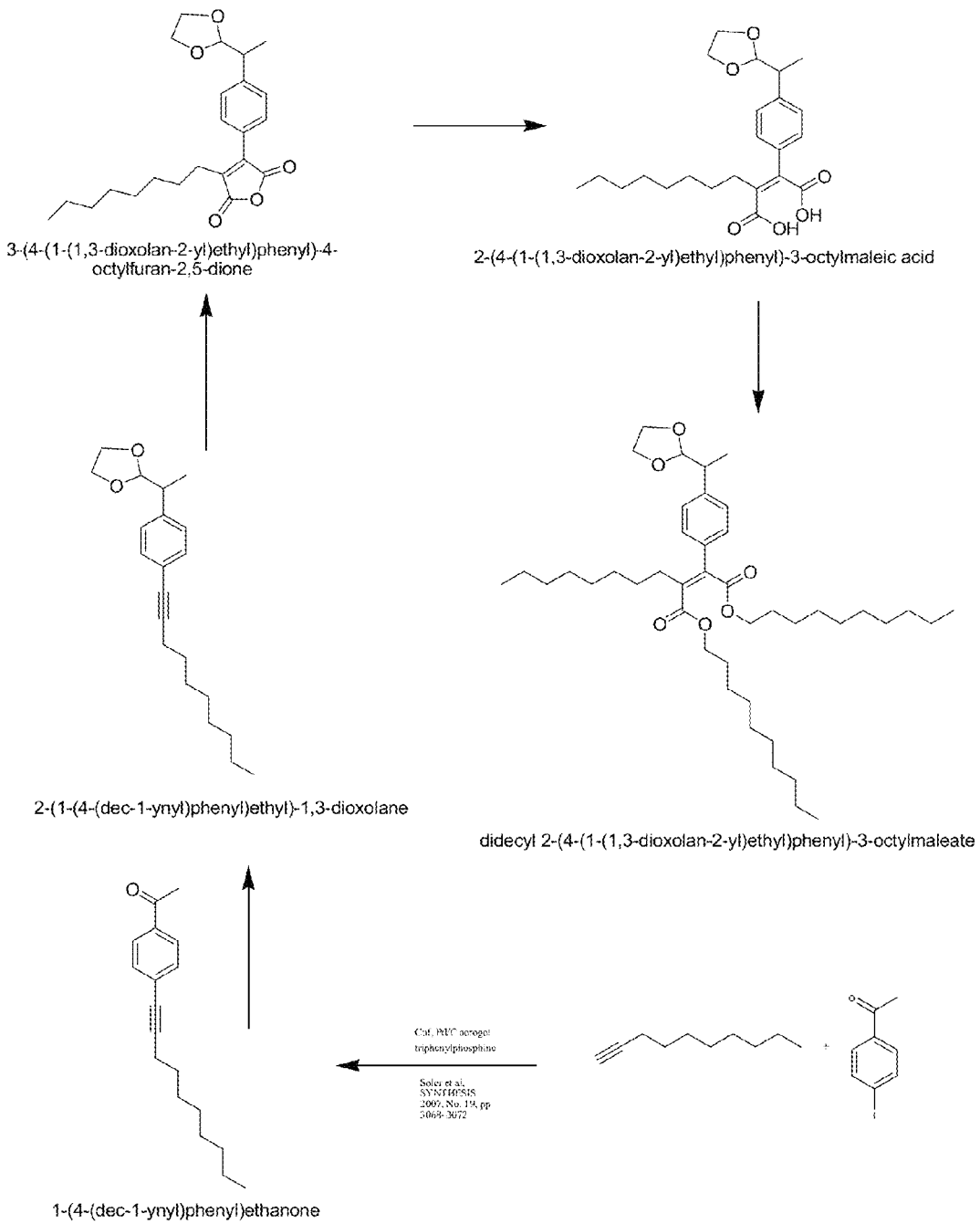
FIGS. 9-11 are an illustration of the steps of, and associated changes in the chemical structure of compounds used in the preparation of substituted glyoxal for coupling with coelenterazine.
Figure 10:
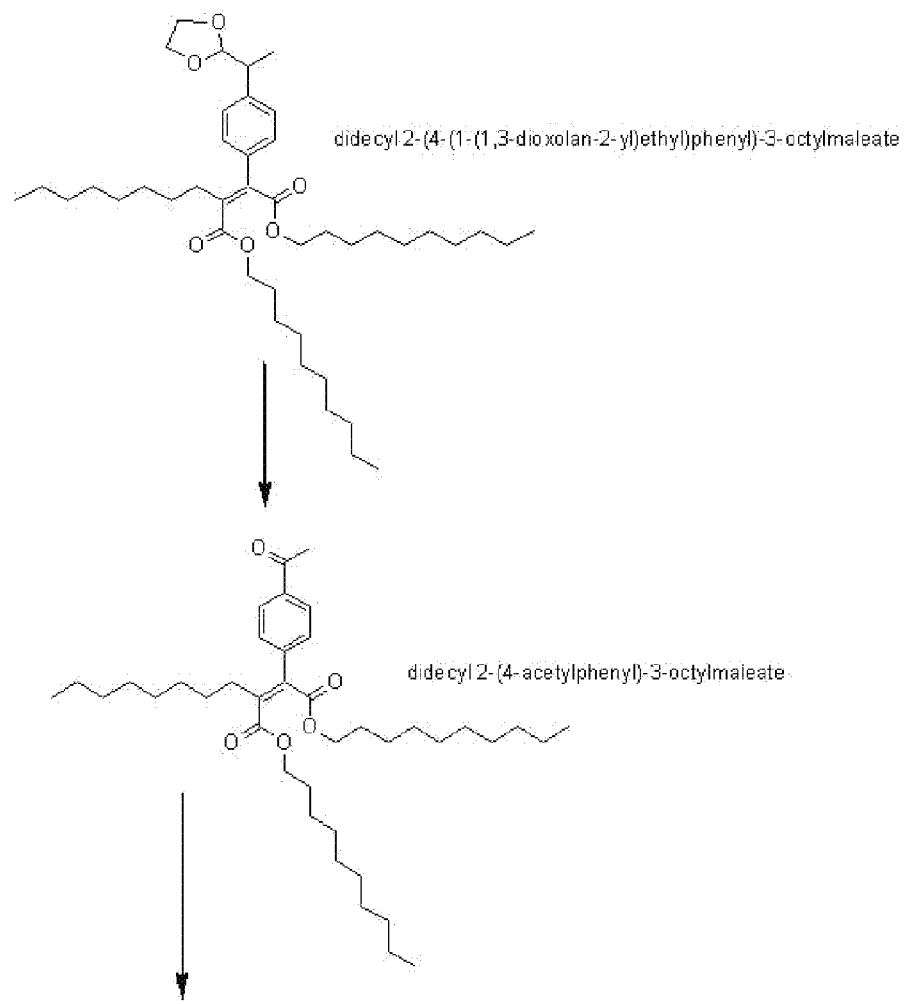
Figure 11:
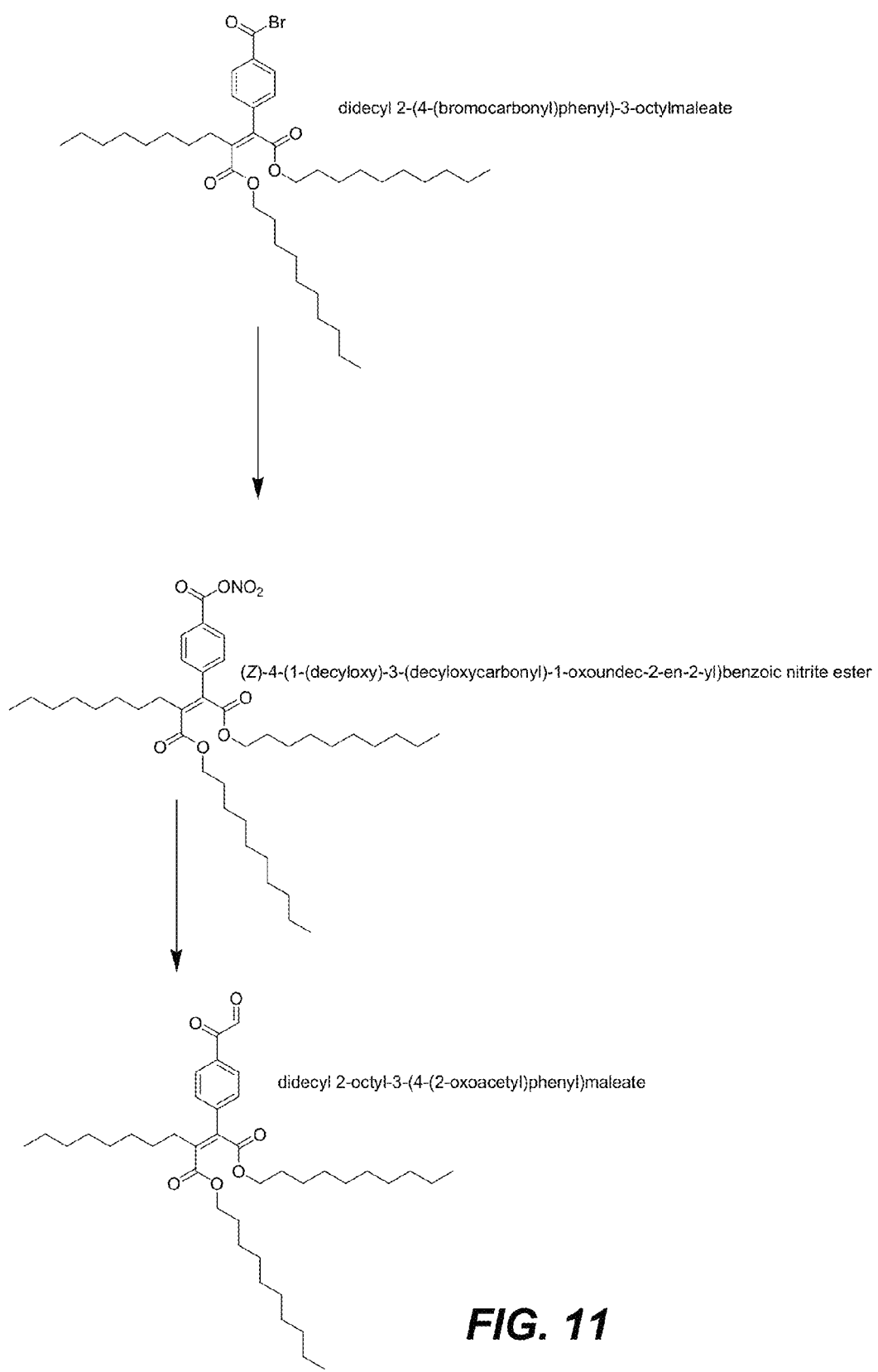

The procedure for the preparation of substituted glyoxal for coupling with coelenterazine is shown generally in FIGS. 9, 10, and 11 and is specifically described in the following Example.

Glyoxal Synthesis Step 1

Figure 12:
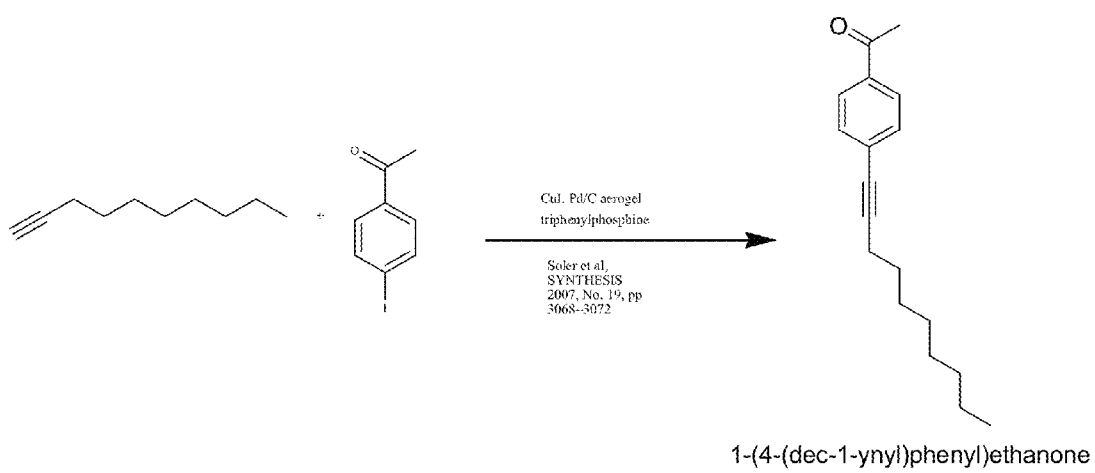
FIG. 12 is an illustration of glyoxal synthesis step 1 used in the preparation of substituted glyoxal for coupling with coelenterazine.

Glyoxal synthesis step 1 is shown in FIG. 12. In a 100 mL Schlenk tube containing 46% Pd—C aerogel (110 mg, 0.47 mmol) were placed CuI (190 mg, 1 mmol), $Ph_3P$ (250 mg, 1 mmol), 4-iodoacetophenone (0.79 mmol), i-$Pr_2NH$ (0.17 mL, 1.2 mmol), deca-1-yne (8 mmol), and previously degassed dimethylformamide (DMF) (0.5 mL) under argon. This was magnetically stirred at 100° C. for a 16-h period. After cooling, the solution was removed and the catalyst was washed with DMF (3×3 mL) and recovered. The combined organic extracts were diluted in $Et_2O$ (100 mL), washed with brine (3×30 mL), dried (annh. $MgSO_4$), and evaporated at reduced pressure. The residue (a yellow oil) was purified by preparative high pressure column chromatography (silica gel, n-hexane-EtOAc, 99.5:0.5) to give the product, 1-(4-(dec-1-ynyl) phenyl)ethanone as a yellow oil; yield: 96% $^1H$ NMR ($CDCl_3$): d=7.87 d,(2 H), 7.53 (d, 2 H), 2.55 (s, 3 H), 2.03 (2 H), 1.46 (2 H), 1.31 (m, 10 H), 0.86 (3 H) 13C NMR ($CDCl_3$): d=CH3,14.0; CH2 22.6; CH2 31.5,; CH2 29.3; CH2 28.7; CH2 28.4; CH2 28.7; CH2 18.7; C (alkyne) 100.1; C (alkyne) 78.5; CH3 29.3; C (carbonyl) 199.8; C 136.4; CH 128.4; CH 132.2; C 127.1; CH 132.2; CH 128.4

Glyoxal Synthesis Step 2

Figure 13:
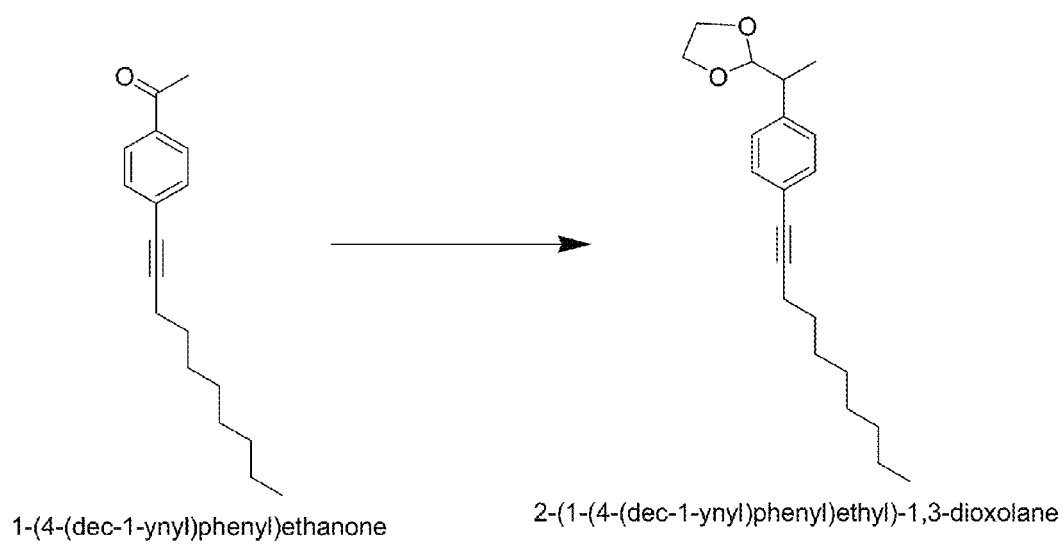
FIG. 13 is an illustration of glyoxal synthesis step 2 used in the preparation of substituted glyoxal for coupling with coelenterazine

Glyoxal synthesis step 2 is shown in FIG. 13. The Compound is protected using method of N. H. Andersen and H.-S. Uh, *Synth. Commun.*, 3, 125 (1973); glycol (1.1 mole), oxalic acid (2 mole equivalents) acetonitrile at 25 C for 1 hour. Workup; extraction with ethyl acetate (3×), extract with 1% solution of Girard's reagent P, wash with 8× of water, dry over annhydrous Magnesium sulfate, rotovap (Buchi) to yield oil, flash purify oil through a small column of silica gel. $^1H$ NMR ($CDCl_3$): d=7.34 d,(2 H), 7.13 (d, 2 H), 5.27 (1H), 3.85, 3.95 (m, 4H) 3.59 (1H) 2.55 (s, 3 H), 2.03 (2H), 1.46 (2H) 1.30 (m, 10 H), 0.86 (3 H). H), 1.31 (m, 10 H), 0.86 (3 H).

Glyoxal Synthesis Step 3

Figure 14:
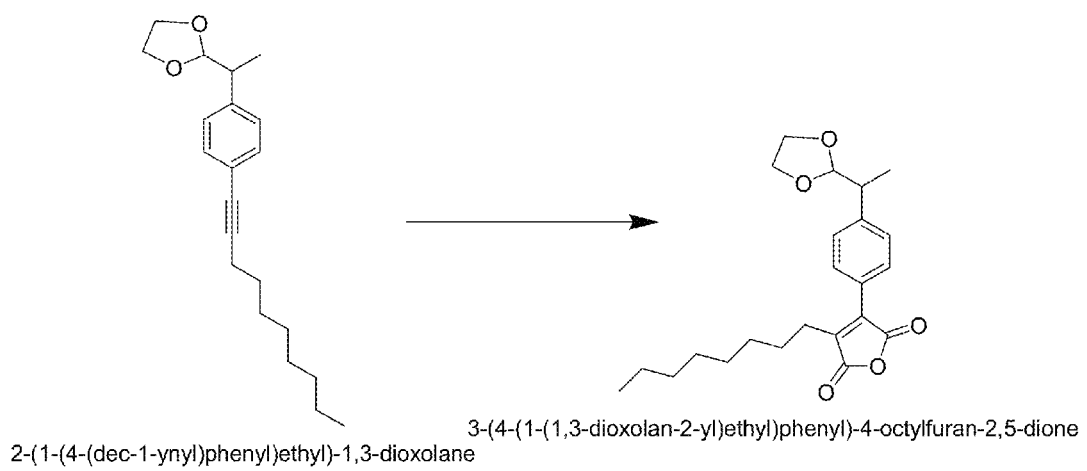
FIG. 14 is an illustration of glyoxal synthesis step 3 used in the preparation of substituted glyoxal for coupling with coelenterazine

Glyoxal synthesis step 3 is shown in FIG. 14. The electrocarboxylation with $CO_2$ is carried out in a high-pressure stainless-steel undivided cell designed to fit into a modified Paar bomb equipped with electrical feedthroughs. The electrolytic cell is fitted with a nickel sheet (3 cm×4 cm×0.05 cm) as the cathode and an aluminum (or magnesium) plate (3 cm×4 cm) as the anode, Prior to the electrolysis, the two electrodes were cleaned with detergent and diluted HCl, washed with distilled water. n-Bu$_4$NBr (10 mmol), dried DMF solvent (100 mL), and 2-(1-(4-(dec-1-ynyl)phenyl)ethyl)-1,3-dioxolane (6.28 gm, 20 mmol) are added to the cell. Carbon dioxide is then charged into the bomb after the cell was sealed. The electrolysis was performed at a suitable constant current until 4 F per mole of starting substrates had been passed through the cell at room temperature. The electrolyte solution was continuously stirred by a magnetic stirrer during the electrolysis. At the end of the electrolysis, the solvent was removed at reduced pressure, and the residue was acidified with dilute HCl and extracted with diethyl ether. The ether phase was washed twice with distilled water. After evaporation of ether, the product was purified by flash chromatography. Yield 80% $^1$H NMR (CDCL$_3$): CH 7.26 (aromatic); CH2 3.90 and CH4.90 (1,3-dioxolan); CH3 0.86; CH2 1.37 (14H) CH 1.50 $^{13}$C NMR 165.9; 165.1; 147.7; 143.7; 141.0; 137.4; 129.7; 128.5; 126.0; 108.8; 66.8; 38.4; 31.8; 29.7; 27.1; 24.3; 22.5; 14.1 11.5

Glyoxal Synthesis Step 4

Figure 15:
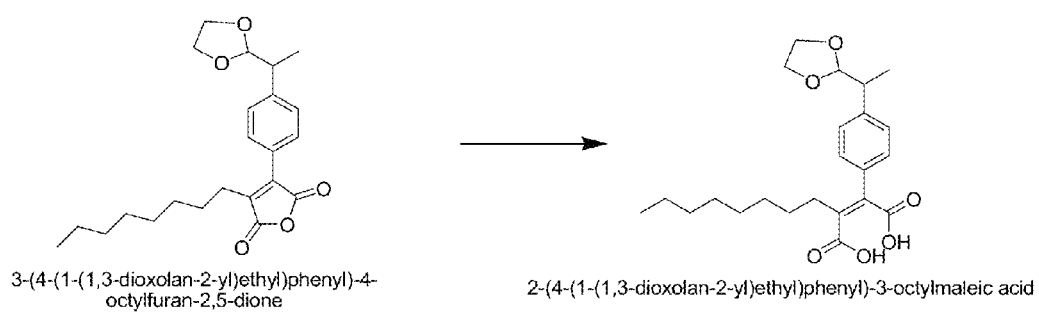
FIG. 15 is an illustration of glyoxal synthesis step 4 used in the preparation of substituted glyoxal for coupling with coelenterazine

Glyoxal synthesis step 4 is shown in FIG. 15. The acid is formed from the anhydride by means of warming in dilute LiOH. The dilithium salt is recrystallized from warm isopropanol-water. The NMR was not taken. In the LC/MS, compound (dilithium salt) gave m/e: 416.24 (100.0%) and some smaller decomposition peaks.

Glyoxal Synthesis Step 5

Figure 16:
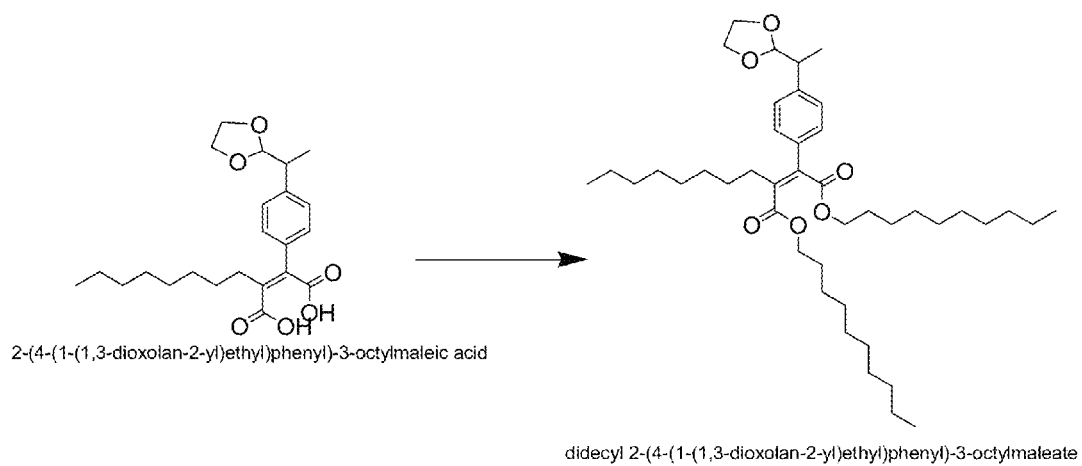
FIG. 16 is an illustration of glyoxal synthesis step 5 used in the preparation of substituted glyoxal for coupling with coelenterazine

Glyoxal synthesis step 5 is shown in FIG. 16. The ester is prepared from the acid chloride. The acid chloride is prepared by the procedure of Cvetovich and DiMichele, *Organic Process Research & Development* 2006, 10, 944-946, from the dilithium salt. A small amount (0.2 mole equivalent) of Cesium carbonate is present as a catalyst. The reaction mixture is added to 1% sodium bicarbonate, extracted 3× with ethyl acetate, and the extracts pooled, dried with magnesium sulfate, and reduced on the rotary evaporator to a thick oil. The material is chromatographed on Silica gel (ethyl acetate-heptane) to give purified ester, yield 71%, TLC, single spot. Mass spectrum: m/e: 684.53 (100.0%) $^1$H NMR (CDCL$_3$): 7.26 (m, 3H), 7.08 (m, 3H), 5.27 (1H), 3.9 (m, 4H), 3.90 (m, 4H), 1.96 (m, 2H), 1.56 (m, 4H), 1.37, singlet and multiplet (46H), 0.86 (9H) $^{13}$C NMR: 168.2; 167; 166.0; 147; 141.9; 139.2; 129,7; 126.2; 108.2; 66.8; 65.6; 31.8 29.7; 27.1; 29.4; 25.8; 22.7; 14.1

Glyoxal Synthesis Step 6

Figure 17:
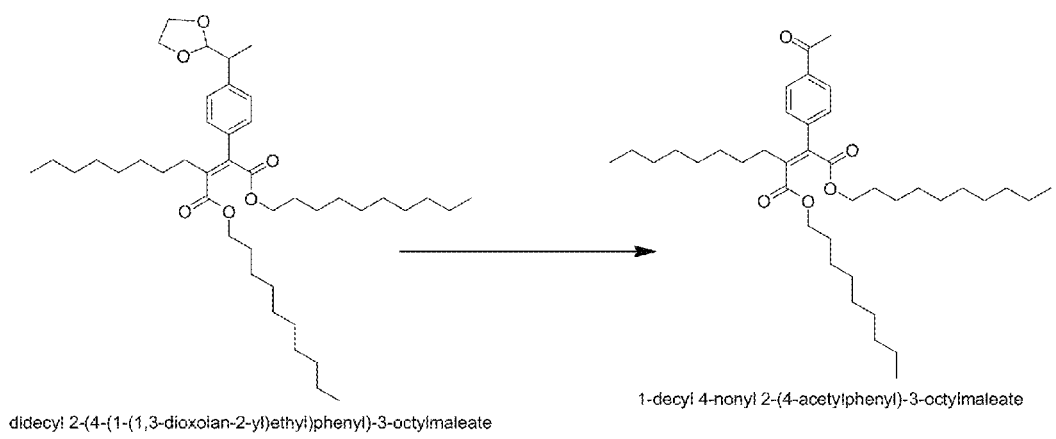
FIG. 17 is an illustration of glyoxal synthesis step 6 used in the preparation of substituted glyoxal for coupling with coelenterazine

Glyoxal synthesis step 6 is shown in FIG. 17. Deprotection of the glyoxal is achieved with pyridinium tosylate in acetone at 25° C. in a quantitative manner.

Glyoxal Synthesis Step 7

Figure 18:
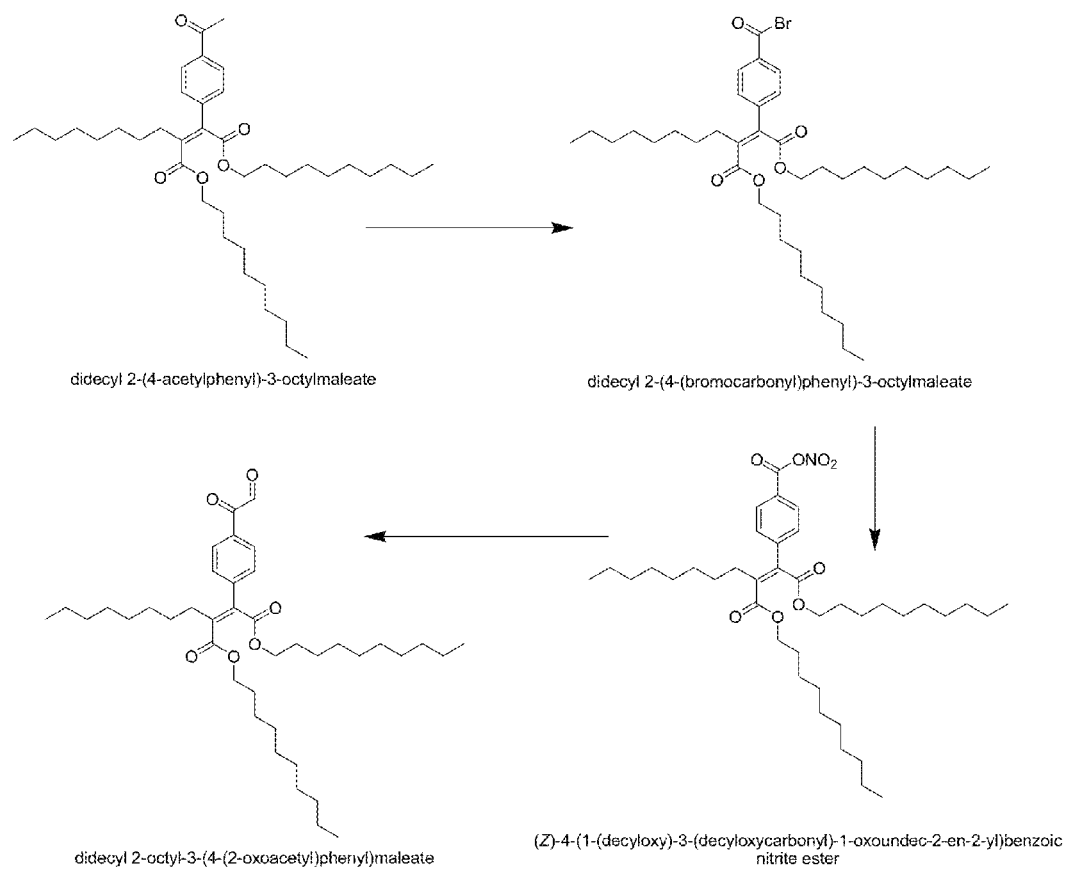
FIG. 18 is an illustration of glyoxal synthesis step 7 used in the preparation of substituted glyoxal for coupling with coelenterazine

Glyoxal synthesis step 7 is shown in FIG. 18.

K. Use of Bioluminescence Generating Systems on Test Subjects

Instillation of a bioluminescent solution into the bile duct, intestinal anastomosis, or ureter during surgery allows excellent instantaneous visualization to the surgeon, potentially preventing damage to these structures. These techniques may also facilitate recognition of leaks or injuries, greatly expediting the surgical procedure. This visualization may be performed using a conventional endoscope or in some methods a modified cooled CCD or CMOS camera specifically adapted for these procedure. These methods are not limited to the above examples, but rather can be applied to any anatomic tube, duct, lumen, vessel, chamber or hollow structure.

One embodiment of the invention includes the viewing of bioluminescent illumination with a red light background in order that background anatomy with visible light can be viewed at the same time as the bioluminescent image. In terms of human vision, this is optimal if a green signal, generated by the bioluminescent system, and a red signal, generated by a lamp or an LED, are used (Nathans J (1999)). The evolution and physiology of human color vision: insights from molecular genetic studies of visual pigments. *Neuron:* 299-312. This is accomplished with the aid of a conventional color endoscope camera which has two narrow band interference filters. Endoscopes equipped with interference filters are well known in the prior art for the protection of the surgeon to filter out light from a YAG laser when using this laser for cutting through the endoscope (U.S. Pat. No. 4,916,534, Endoscope, Apr. 10, 1990). Endoscopes with rotating interference filters have been used to remove infrared light from the illuminating lamp (U.S. Pat. No. 5,993,037, Light Source Device for Endoscopes, Nov. 30, 1999). Endoscopes used for fluorescent studies, such as cystoscopes in the bladder, have been equipped with interference filters to isolate the fluorescence signal (U.S. Pat. No. 5,984,861 Endofluorescence Imaging Module For An Endoscope, Nov. 16, 1999).

As to the requisite interference filters, the construction of such filters is well known in the prior art in the visible regions of the electromagnetic spectrum (U.S. Pat. No. 2,890,624, Interference Color Filter With Blue Absorbing Layers Jun. 16, 1959) and infrared (U.S. Pat. No. 4,832,448, Interference Filters May 23, 1989). A dichroic mirror could alternatively be employed in order to reduce the total amount of undesired light admitted in to the system (U.S. Pat. No. 4,047,805, Ripple-Free Dichroic Mirrors, Sep. 13, 1977). Specific bands could also be eliminated if desired (U.S. Pat. No. 5,400,174 Optical Notch Or Minus Filter Mar. 21, 1995) although broadband filters are to be most preferred. The filters could be located at the viewer's end, such as in the glasses of the surgeon (U.S. Pat. No. 6,369,964 Optical Filters For Reducing Eye Strain, During Surgery Apr. 9, 2002) but this is not a highly preferred method because the resolution of the system should be higher if light filtering is done prior to conversion to an electronic signal by the camera. In summary, it is seen that the use of various wide and narrow band interference and dichroic filters is a well known method in the Prior Art to separate a red signal (illuminating the interior of the anatomical structure) from the blue-green signal provided by the bioluminescent composition.

As to the required source of red light, it could be obtained from a conventional high pressure xenon arc lamp by means of conventional interference filters (U.S. Pat. No. 6,364,829 Autofluorescence Imaging System For Endoscopy Apr. 2, 2002) but is probably most conveniently obtained by the use of a light emitting diode. Recent work in this area has provided high-output narrow band devices which do not have temperature sensitivity or wavelength limitations, an issue with some older devices. For example, see U.S. Pat. No. 6,829,271, Light-Emitting Semiconductor Device Producing Red Wavelength Optical Radiation, Dec. 7, 2004; U.S. Pat. No. 7,071,490 Group Iii Nitride Led With Silicon Carbide Substrate Jul. 4, 2006). These devices are small and can readily be incorporated into the endoscopic probe which enters the patient. The advantage which this presents is that the fiber-optical assembly is not needed to carry the incoming visible or infrared light signal. Indeed, in one modification of the endoscope which is useful in the present context both the camera and the red light source could be located on a trocarlike probe which would enter a cavity within an organ of the patient, and no fiber optical whatsoever would be required. An advantage of a conventional fiber optic-based endoscope would be that a very low light level image-intensified, cooled CCD camera could be employed. For example, see U.S. Pat. No. 7,129,464 Low-Photon Flux Image-Intensified Electronic Camera Oct. 31, 2006.

However, our bioluminescent studies in animals in accordance with the present application as described in the specification have provided study results of sufficient brightness that use of a cooled CCD camera has not been necessary, nor has an image intensifier been needed. Indeed, it is a major advantage of the methods and procedures described within the present application that simple commercial video and still cameras of consumer-grade quality are more than sufficient to record the bioluminescent signal, and that generally it is as bright as to be visible with the use of an unmodified, off-the-shelf endoscope. Wavelengths other than the red could be used, provided that the CCD camera had adequate sensitivity in the desired wavelength region. Low light level CCD cameras sensitive in the infrared region are well known in the prior are (for example see U.S. Pat. No. 7,016,518, Vehicle license plate imaging and reading system for day and night, Mar. 21, 2006.) Image intensifiers of Generation III and IV are also commercially available which are extremely sensitive in the near-infrared region of the electromagnetic spectrum.

The membrane permeant analogs of coelenterazine concentrate in hydrophobic regions of various organs, in particular including the central nervous system. The blood-brain barrier (BBB) is an endothelial barrier present in capillaries that course through the brain. A very complex tight-junctional epithelium is integral to this barrier. The BBB significantly impedes entry from blood to brain of virtually all molecules, except those that are small and lipophilic. Certain small molecules and rather surprisingly some very large molecules can readily cross the blood brain barrier in an efficient manner. Except for small hydrophobic molecules which can bind to albumin they do so by active transport. Amino acids which are of course required in the brain are moved across the barrier by a series of specific transporters (Hawkins, R. A., R. L. O'Kane, et al. (2006). "Structure of the blood-brain barrier and its role in the transport of amino acids." *Journal of Nutrition* 136(1 Suppl): 218S-26S.). Most large molecules are moved across the BB by receptor-mediated transport. The best known of these is the transferrin receptor but evidence indicates that other growth factors and cytokines such as ferritin (Fisher, J., K. Devraj, et al. (2007). "Ferritin: a novel mechanism for delivery of iron to the brain and other organs." *American Journal of Physiology—Cell Physiology* 293(2): C641-9) and TGF-beta can cross the BBB (McLennan, I. S., M. W. Weible, 2nd, et al. (2005). "Transport of transforming growth factor-beta 2 across the blood-brain barrier." *Neuropharmacology* 48(2): 274-82). One of the more important transporters is P-glycoprotein, also present in relatively high concentrations on brain capillaries. (Sanderson, L., A. Khan, et al. (2007). "Distribution of suramin, an antitrypanosomal drug, across the blood-brain and blood-cerebrospinal fluid interfaces in wild-type and P-glycoprotein transporter-deficient mice." *Antimicrobial Agents & Chemotherapy* 51(9): 3136-46.) That is, it generally transports back into the blood a variety of lipophilic molecules that enter the brain and is in maintaining therapeutic concentrations of drugs in the brain (Parepally, J. M., H. Mandula, et al. (2006). "Brain uptake of nonsteroidal anti-inflammatory drugs: ibuprofen, flurbiprofen, and indomethacin." *Pharmaceutical Research* 23(5): 873-81). Various therapeutic strategies have been devised to couple drugs to peptides and even proteins which carry them across the BBB by carrier-mediated transport (de Boer, A. G. and P. J. Gaillard (2007). "Strategies to improve drug delivery across the blood-brain barrier." *Clinical Pharmacokinetics* 46(7): 553-76.). The important point is that very hydrophobic, non-charged small molecules which bind to albumin will be generally transported efficiently across the blood brain barrier provided that they are not back-transported by the P-glycoprotein receptor. (Pardridge W. M., and Mietus, L. J. (1979) Transport of Steroid Hormones through the Rat Blood-Brain Barrier *J. Clin. Invest.* 64:145). In the present study, we prepared hydrophobic analogues of coelenterazine which bind to albumin and are efficiently transported across the blood-brain barrier. Such analogues can bind efficiently to the tissues of the lymphatics, making the sentinel node detection possible.

In fact we have found that sentinel node analysis may be performed utilizing coelenterazine and membrane permeant analogs of coelenterazine. We have found that coelenterazine and membrane permeant analogs of coelenterazine can be used for the bioluminescent analysis of lymphatic connection to the sentinel node of a tumor. To do this, the enzyme luciferase, typically but not limited to that from *Renilla reniformis*, is injected into the lymphatics which surround the tumor in the manner that technetium colloid or blue dye is administered. Then, upon biopsy of the sentinel node, the biopsy specimen is treated with coelenterazine or a membrane permeant analog of coelenterazine. Bioluminescence may be detected using a camera, or a luminometer, or by visual inspection.

Use of bioluminescence systems in connection with sentinel node analysis will be enhanced by mixing one of the components of the bioluminescence system with sugars or other molecules that are absorbed by cancer cells at a more rapid rate than surrounding tissues.

Clinical tests using bioluminescence systems as described in this application are described in the following examples.

EXAMPLE 1

Figure 19:
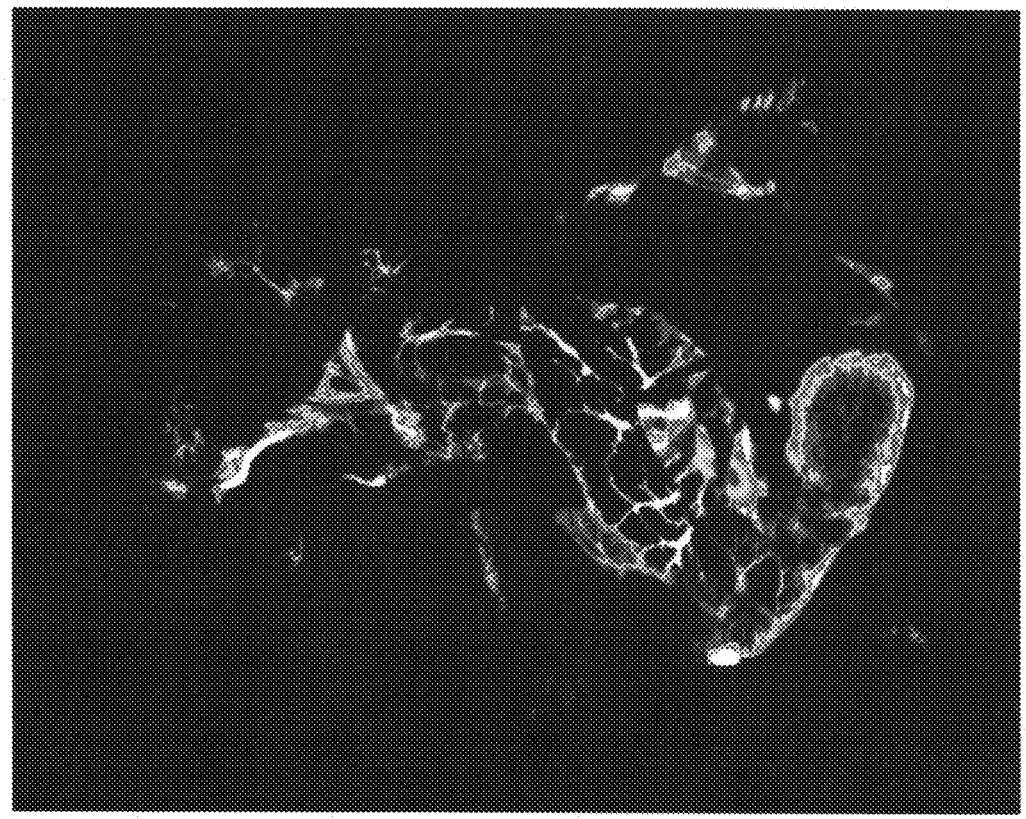
FIG. 19 is a photograph showing a rat which has been administered with bioluminescent compounds in accordance with the present invention.

A rat was equipped with bilateral jugular cannulas. To one was applied a solution of coelenterazine (50 mM) in Hank's balanced salt solution and to the opposite jugular cannula was administered *Renilla* luciferase, 5 mg/ml in Hank's balanced slat solution. An image was obtained and was pseudocoloured with Scion Image according to the light level obtained by a Princeton Instruments camera and is shown at FIG. 19.

EXAMPLE 2

Figure 20:
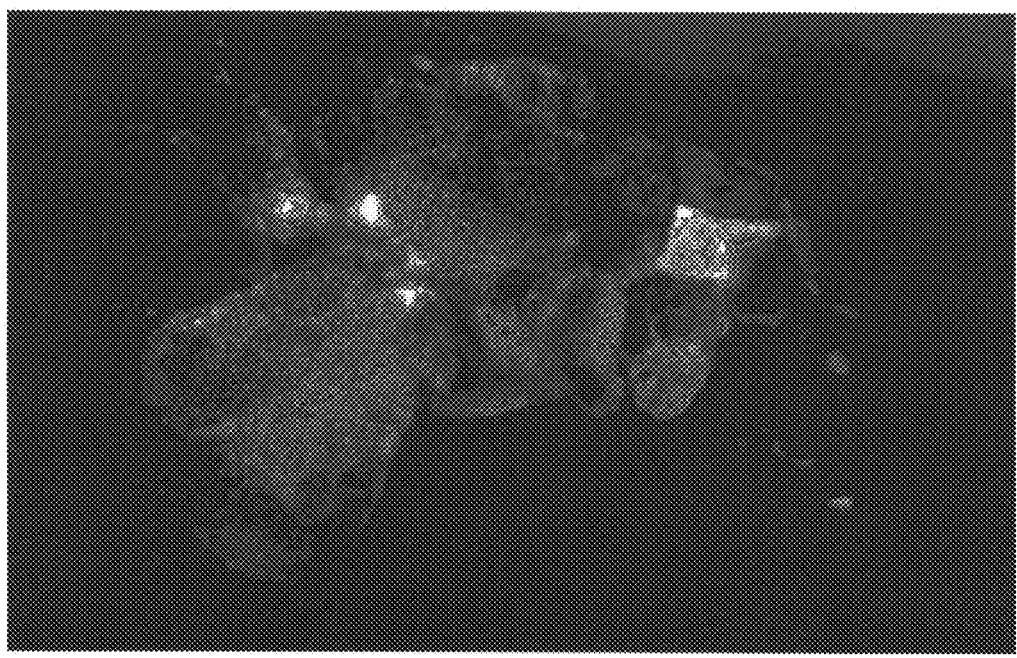
FIG. 20 is a photograph showing a rat liver which has been administered with bioluminescent compounds in accordance with the present invention.

A rat was equipped with bilateral jugular cannulas. To one was applied a solution of coelenterazine (50 mM) in Hank's balanced salt solution and to the opposite jugular cannula was administered *Renilla* luciferase, 5 mg/ml in Hank's balanced slat solution. An image was obtained and was pseudocoloured with Scion Image according to the light level obtained by a Princeton Instruments camera and is shown at FIG. 20. FIG. 20 illustrates patchy contrast regions in the liver:

EXAMPLE 3

Figure 21:
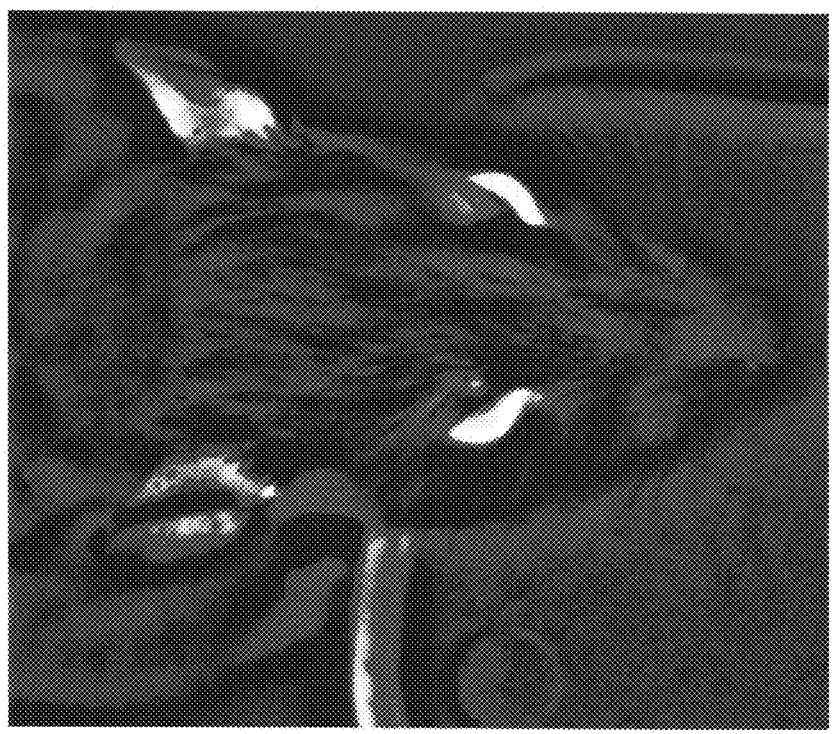
FIG. 21 is a photograph showing a head of a rat which has been administered with bioluminescent compounds in accordance with the present invention.

A rat was equipped with bilateral jugular cannulas. To one was applied a solution of coelenterazine (50 mM) in Hank's balanced salt solution and to the opposite jugular cannula was administered *Renilla* luciferase, 5 mg/ml in Hank's balanced slat solution. An image was obtained and was pseudocoloured with Scion Image according to the light level obtained by a Princeton Instruments camera and is shown at FIG. 21. FIG. 21 perfusion of bioluminescence in the whole animal:

EXAMPLE 4

Figure 22:
FIG. 22 is a photograph showing a duodenal loop of a rat which has been administered with bioluminescent compounds in accordance with the present invention.

A duodenal loop in the rat was cannulated and the bioluminescent generating mixture was applied thereto. An image was obtained and was pseudocoloured with Scion Image according to the light level obtained by a Princeton Instruments camera and is shown at FIG. 22.

EXAMPLE 5

Figure 23:
FIG. 23 is a photograph showing the duodenum of a rat which has been administered with bioluminescent compounds in accordance with the present invention.

Two separate cannulas were applied to the duodenum of the rat, and luciferase was administered through one and luciferin through the other under the conditions of example 1. An image was obtained and was pseudocoloured with Scion Image according to the light level obtained by a Princeton Instruments camera and is shown at FIG. 23.

EXAMPLE 6

Swine studies. All animal study protocols were approved by the appropriate IACUC, either at the University of Arizona in Tucson, or at the High Quality Research facility located in Ft. Collins, Colo. For these studies, one live pig, approximately 30 kg (anesthetized, non-survival, Arizona site) and one fresh cadaver pig, approximately 30 kg (heparinized, euthanized, Colorado site) were used. A standard open laparotomy operative approach was done to allow use of more than one camera at a time. The color cooled CCD camera used was a Spot R3 supplied by Diagnostic Instruments Inc., Sterling Heights, Mich. This camera is connected by a firewire connection to laptop running Windows XP. The camera is cooled electronically, with its own power source and fan. The camera is controlled and settings adjusted with a Beta Version of the Spot Camera software. Focus is adjusted at the lens for the focal length chosen, between 1 and 2 feet for the open recordings. The videocamera used was a Sony (Sony DCR-SR200) model, which is a hand held camera, mounted on a tripod for the experiments. The image in real time was viewed on the cameras LCD panel or using a small television set. The camera is controlled and settings adjusted on the LCD touch screen. Focus for low light recording is best done in manual mode on the touch screen for the focal length chosen, between 1 and 2 feet for the open recordings.

EXAMPLE 6A

Swine bioluminescent cholangiography was done by direct gallbladder puncture and infusion 40 ccs of bioluminescent media using an 18 gauge angiocatheter. Some retraction on the gallbladder in the same method as for a cholecystectomy was done, specifically lifting and moving the gallbladder cephalad to better expose the neck of the gallbladder—cystic duct junctions. The picture was also converted to monochrome to allow comparison to standard radiologic cholangiogram techniques.

Figure 24:
FIG. 24 is a photograph showing a swine gallbladder as viewed in visible light.
Figure 25:
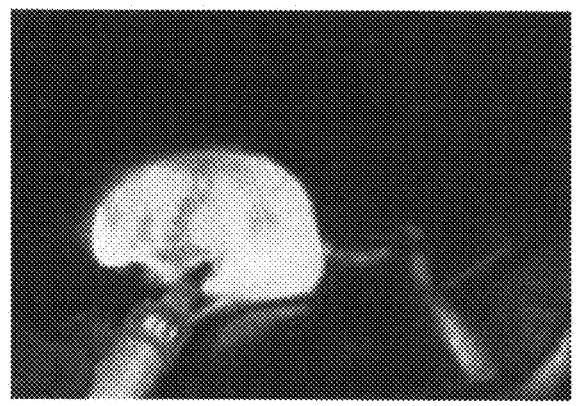
FIG. 25 is a photograph showing a swine gallbladder which has been administered with bioluminescent compounds in accordance with the present invention.
Figure 26:
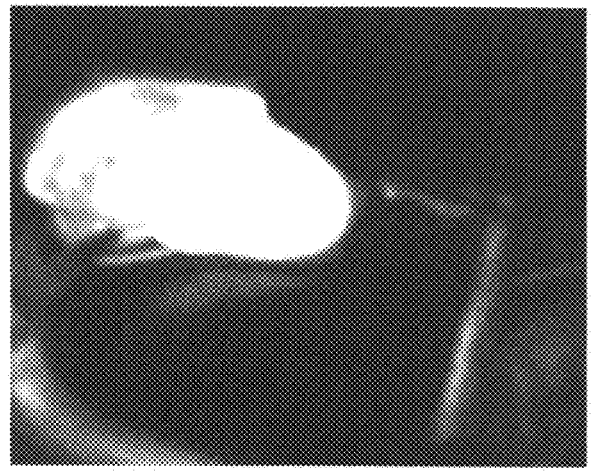
FIG. 26 is a monochrome photograph showing a swine gallbladder which has been administered with bioluminescent compounds in accordance with the present invention.
Figure 27:
FIG. 27 is an inverse image monochrome photograph showing a swine gallbladder which has been administered with bioluminescent compounds in accordance with the present invention.

The standard visble light view of a gallbladder (bile ducts not visualized) is shown at FIG. 24. A color bioluminescent cholangiogram is shown at FIG. 25. A monochome biolumi-nescent cholangiogram is shown at FIG. 26. An inverted monochome bioluminescent cholangiogram is shown at FIG. 27.

EXAMPLE 6B

Figure 28:
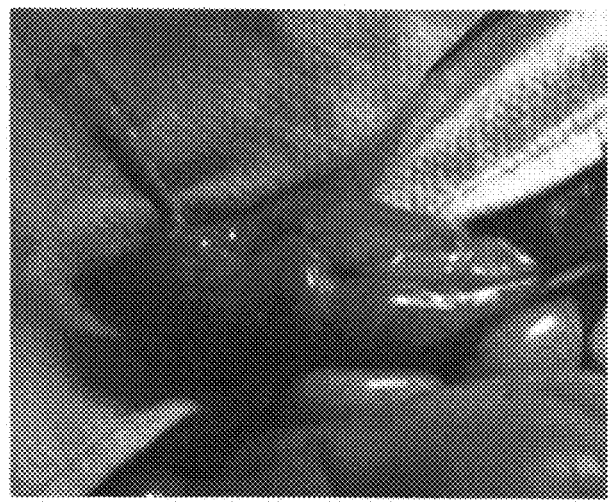
FIG. 28 is a photograph showing a swine bowel anastomosis as viewed in visible light.
Figure 29:
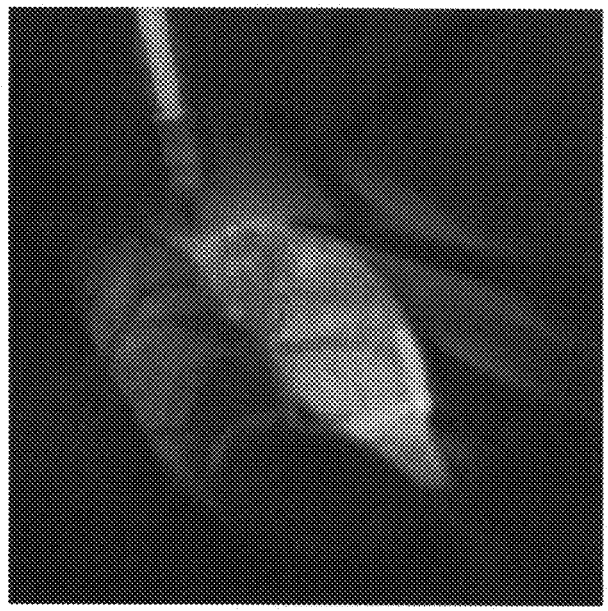
FIG. 29 is a photograph showing a swine bowel anastomosis which has been administered with bioluminescent compounds in accordance with the present invention.

Swine bioluminescent small intestine anastomosis integrity testing was done by direct puncture and infusion of 40 ccs of bioluminescent media using an 18 gauge angiocatheter into the lumen of side to side, stapled small intestine anastomosis. The color cooled CCD camera used was a Spot R3 supplied by Diagnostic Instruments Inc. The standard view of bowel anastomosis is shown at FIG. 28. A color bioluminescent view of bowel anastomosis is shown at FIG. 29.

EXAMPLE 6C

Figure 30:
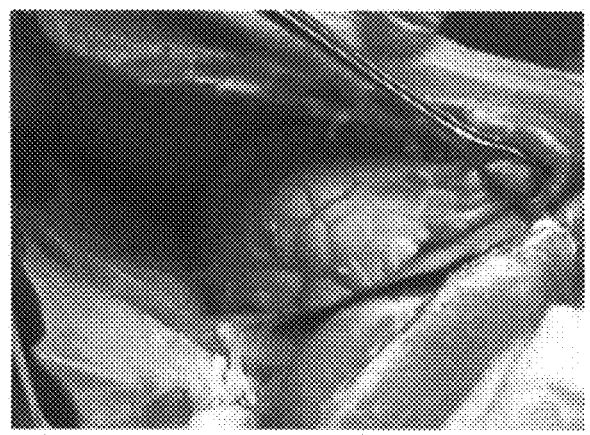
FIG. 30 is a photograph showing a swine lung as viewed in visible light.
Figure 31:
FIG. 31 is a photograph showing a swine lung which has been administered with bioluminescent compounds in accordance with the present invention.
Figure 32:
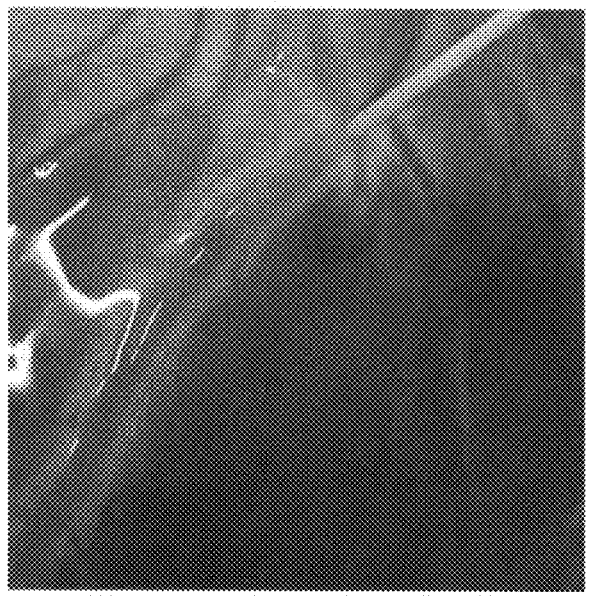
FIG. 32 is a photograph showing a swine heart as viewed in visible light.
Figure 33:
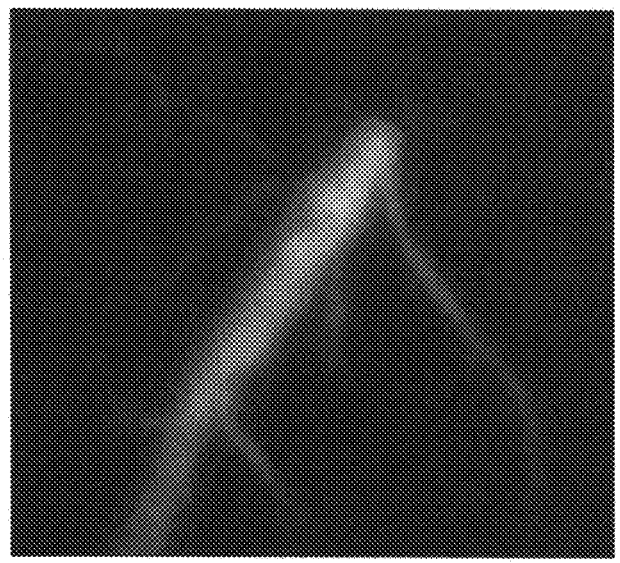
FIG. 33 is a photograph showing a swine heart which has been administered with bioluminescent compounds in accordance with the present invention.
Figure 34:
FIG. 34 is a photograph showing a swine small intestine as viewed in visible light.
Figure 35:
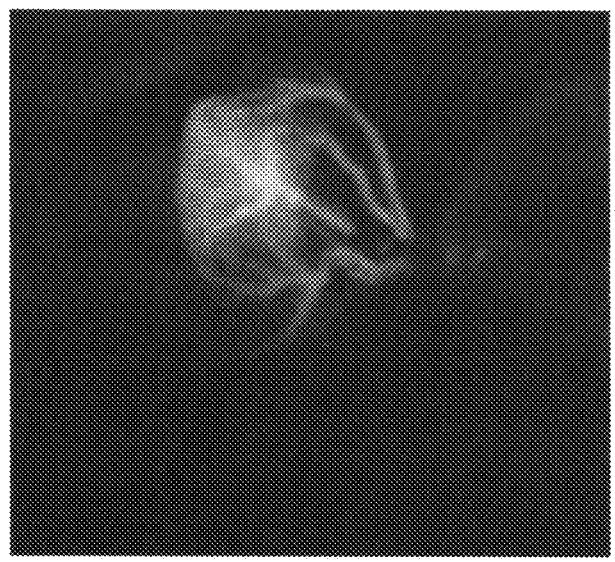
FIG. 35 is a photograph showing a swine small intestine which has been administered with bioluminescent compounds in accordance with the present invention.
Figure 36:
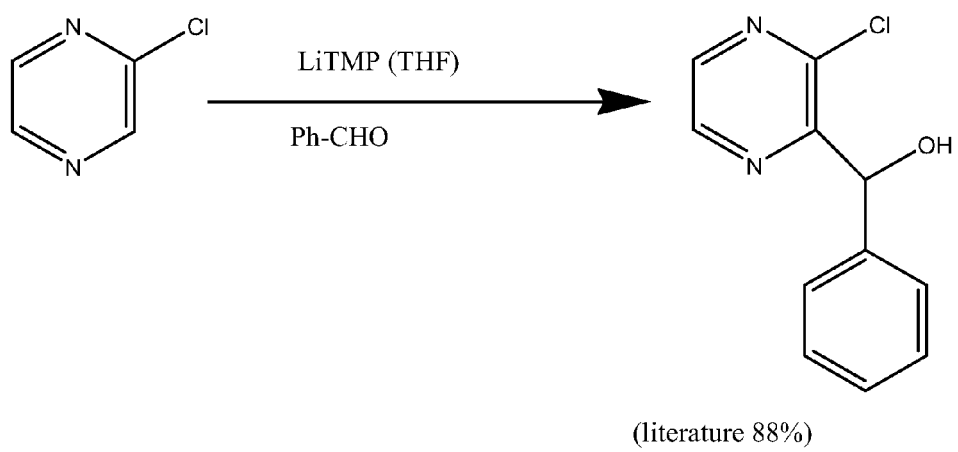
FIGS. 36-39 are an illustration of the steps of, and associated changes in the chemical structure of compounds used in the synthesis of the membrane permeant analogs of coelenterazine illustrated in FIGS. 4-8.
Figure 37:
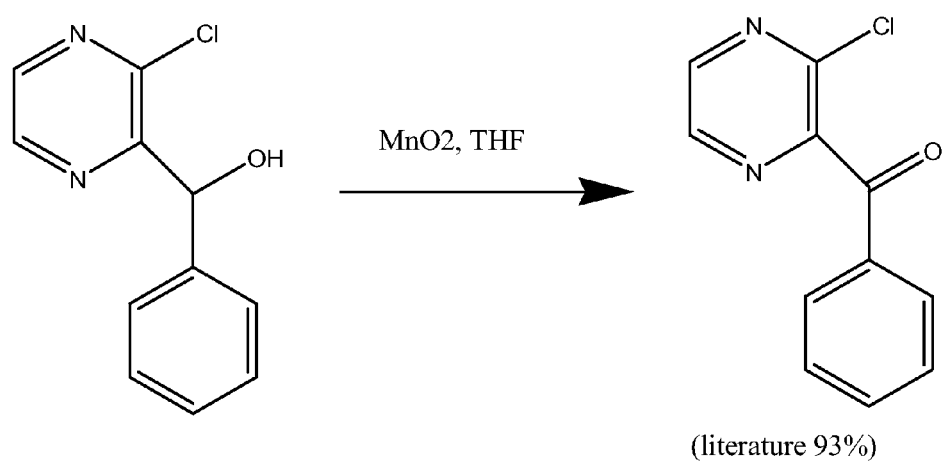
Figure 38:
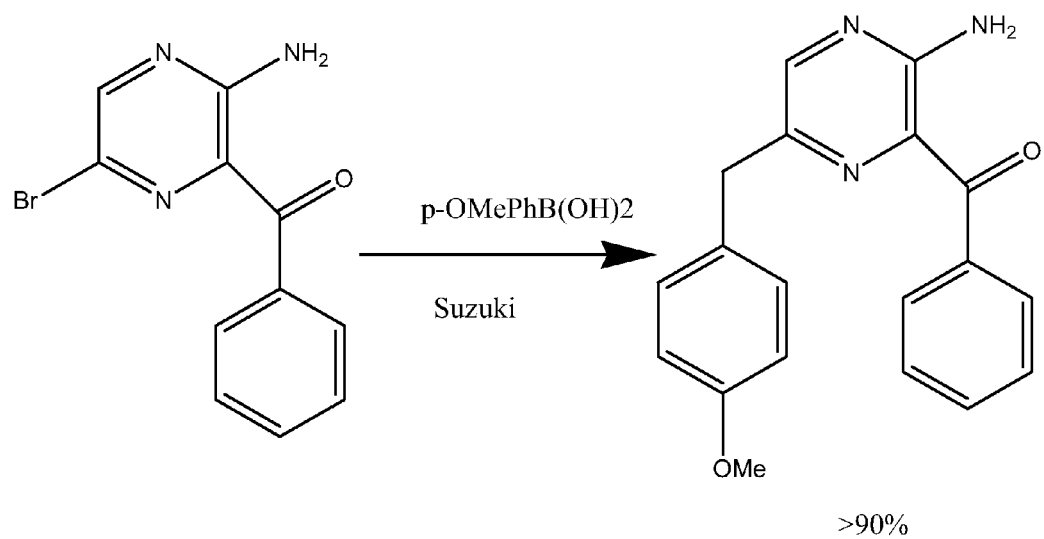
Figure 39:
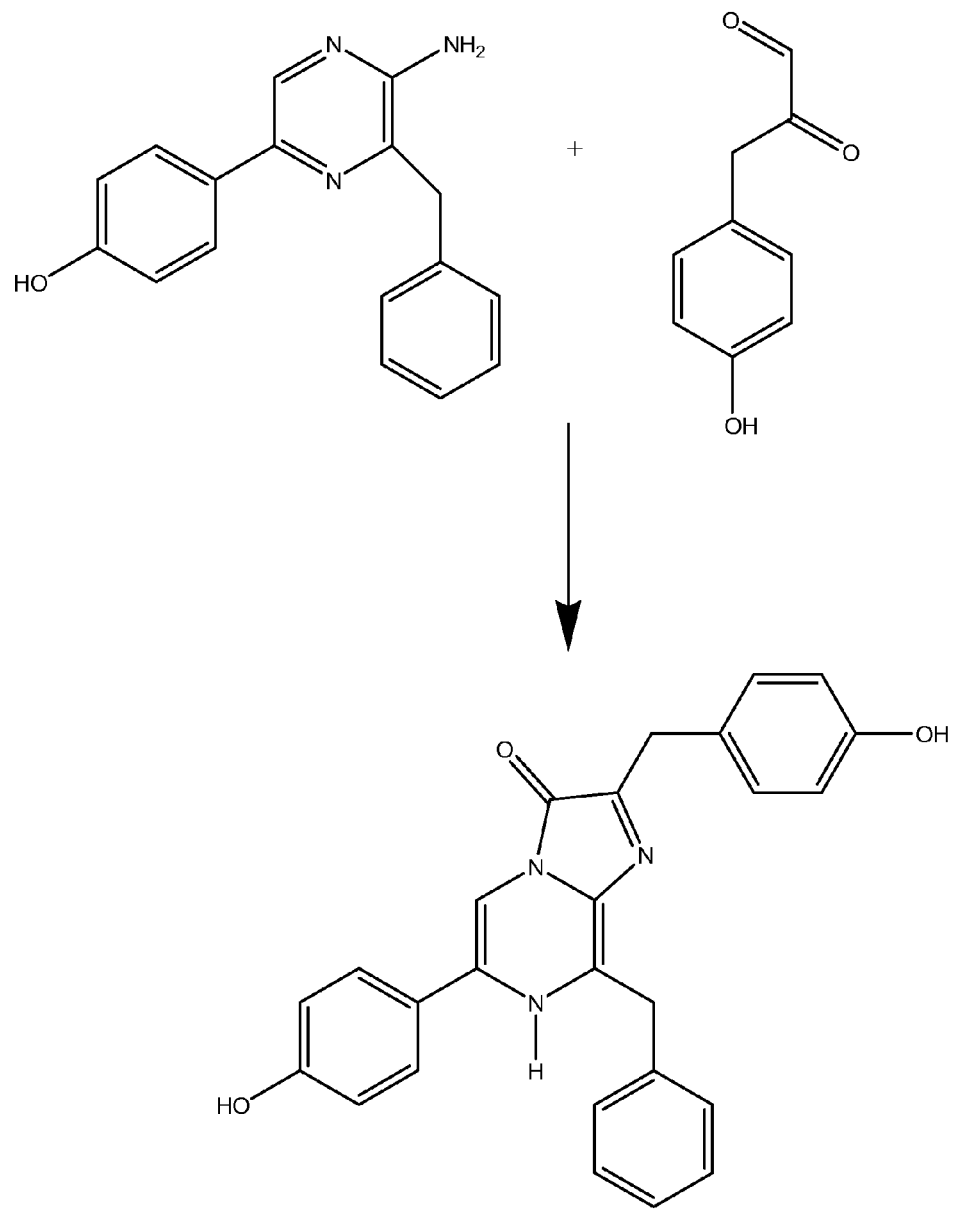

Swine bioluminescent angiography was done was done by direct puncture and infusion of 40 cc of bioluminescent media using an 18 gauge angiocatheter into the pulmonary vasculature, coronary vasculature and small bowel mesentery vasculature, images were from the Sony videocamera. A standard view of the lung right upper lobe is shown at FIG. 30. A color bioluminescent view of the lung right upper lobe is shown at FIG. 31. A standard view of the heart is shown at FIG. 32. A color bioluminescent view of the coronary artery of the heart is shown at FIG. 33. A standard view of the small intestine is shown at FIG. 34. A color bioluminescent view of the mesentery small intestine is shown at FIG. 35.

The foregoing examples establish the value of the present invention in illuminating and highlighting delicate structures.

What is claimed is:

1. A method of using a bioluminescence system to illuminate internal body structures of a subject comprising:

administering to the subject or one or more portions thereof at least one coelenterazine analog selected from the group consisting of Structure II, Structure II

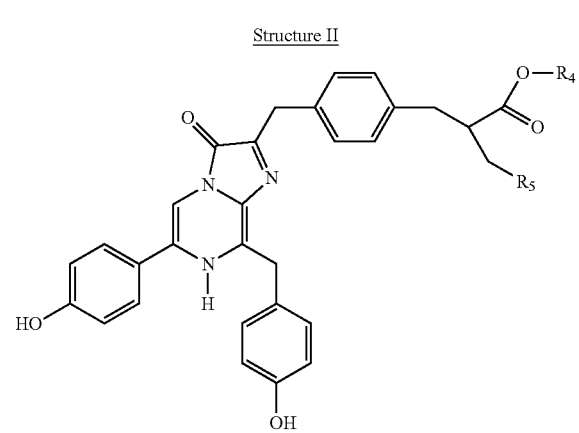

wherein R4 and R5 may independently be alkyl or aralkyl, and R4 may be aryl or optionally substituted aryl, aralkyl or optionally substituted aralkyl, and R5 may be alkyl, optionally substituted alkyl, alkoxy, aralkyl, or optionally substituted aralkyl, aryl, or a heterocycle, Structure III, Structure III

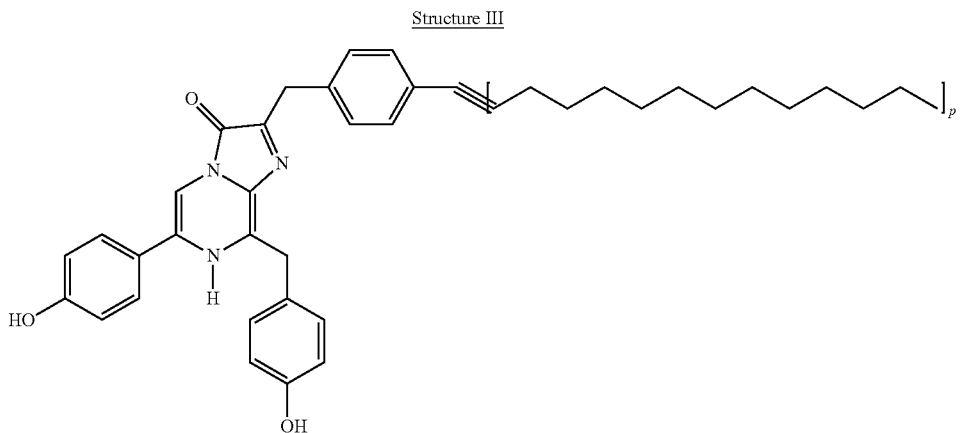

wherein p may be an integer ranging from 1 to 20, and Structure IV,

Structure IV

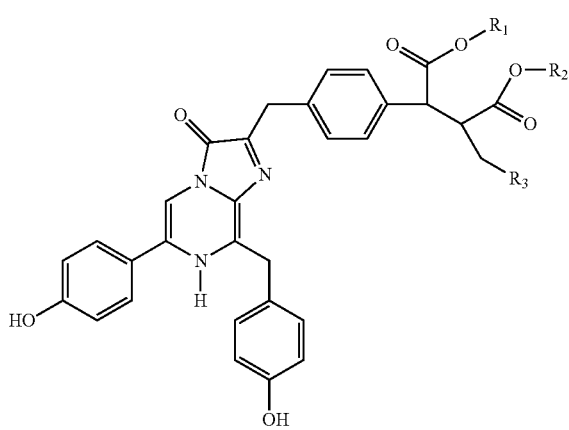

wherein R1, R2, and R3 are independently alkyl, optionally substituted alkyl, alkenyl, or aralkyl; and visualizing and/or imaging said subject or one or more portions thereof.

2. The method of claim 1 wherein said method is used for illumination of one or more components of a circulatory system, nervous system, body organ, or lymphatic system of the subject.

3. The method of claim 2 wherein said one or more components is a hollow viscous.

4. The method of claim 1 wherein the bioluminescence system is used post-operatively to inspect the body structures.

5. The method of claim 1, wherein the step of administering comprises perfusing, administering, injecting, superfusing, infiltrating, or otherwise applying the at least one coelenterazine analog selected from the group consisting of Structure II, Structure II wherein R4 and R5 may independently be alkyl or aralkyl, and R4 may be aryl or optionally substituted aryl, aralkyl or optionally substituted aralkyl, and R5 may be alkyl, optionally substituted alkyl, alkoxy, aralkyl, or optionally substituted aralkyl, aryl, or a heterocycle, Structure III, Structure III

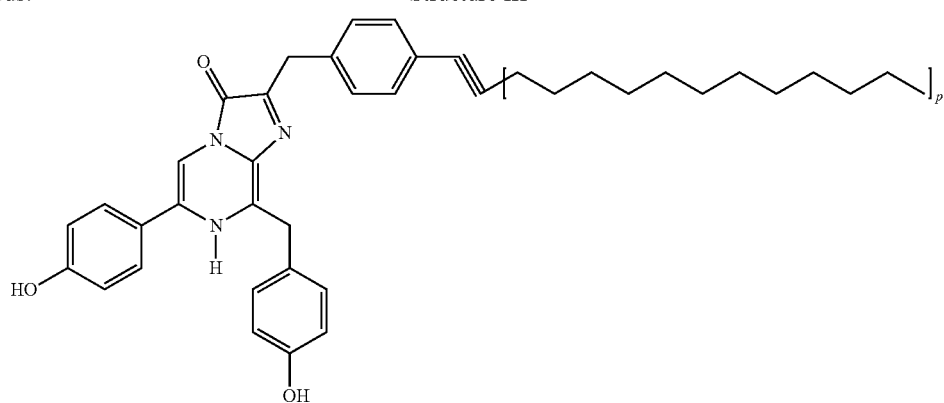

wherein p may be an integer ranging from 1 to 20, and Structure IV,

Structure IV

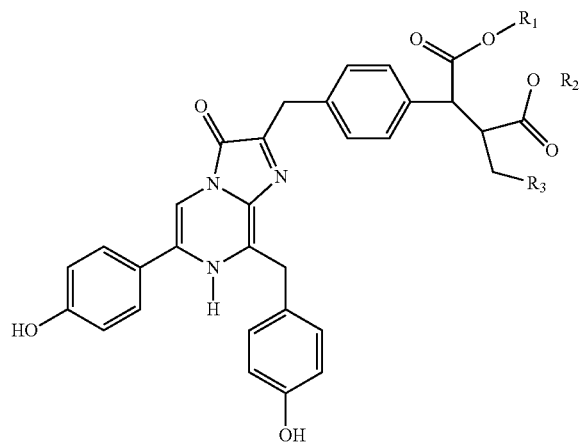

wherein R1, R2, and R3 are independently alkyl, optionally substituted alkyl, alkenyl, or aralkyl, to internal body structures to provide bioluminescent illumination to said body structures; and wherein the step of visualizing and/or imaging comprises obtaining one or more images of said structure with bioluminescent illumination with a camera system sensitive to the wavelength of emission of the bioluminescence system.

6. The method of claim 5, wherein said one or more images are obtained in dim visible light conditions.

7. The method of claim 5, wherein said one or more images are color or monochrome images.

8. The method of claim 5, wherein the step of visualizing and/or imaging further comprises obtaining one or more images of said object with visible light illumination, said visible light comprising visible light in a wavelength range which does not include light in a wavelength range of light emitted by the bioluminescence system.

9. The method of claim 8, wherein said images are obtained with a camera system sensitive to the wavelength of emission of the visible light illumination.

10. The method of claim 9, wherein the visible light illumination is a red light illumination.

11. The method of claim 9, further comprising: comparing said image with bioluminescent illumination with said image with visible light illumination.

12. The method of claim 11 further comprising a step of switching between said image with bioluminescent illumination with said image with visible light illumination.

13. The method of claim 5, wherein the object comprises a component of a animal, avian or human circulatory system, nervous system, body organ, or lymphatic system.

14. The method of claim 13, wherein the object comprises gallbladder, ureter, lung, heart, or intestine.

15. The method of claim 5, wherein said images are obtained by an endoscopic examination of the object.

16. The method of claim 9, wherein said images are obtained by an endoscopic examination of the object.

17. A method of using a bioluminescence system postoperatively to illuminate a surgical tissue in order to inspect the surgical tissue comprising:
administering to the subject or one or more portions thereof a coelenterazine analog selected from the group consisting of Structure II, Structure II

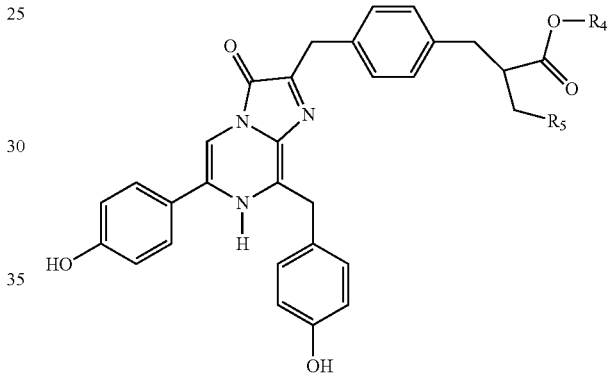

wherein R4 and R5 may independently be alkyl or aralkyl, and R4 may be aryl or optionally substituted aryl, aralkyl or optionally substituted aralkyl, and R5 may be alkyl, optionally substituted alkyl, alkoxy, aralkyl, or optionally substituted aralkyl, aryl, or a heterocycle, Structure III, Structure III

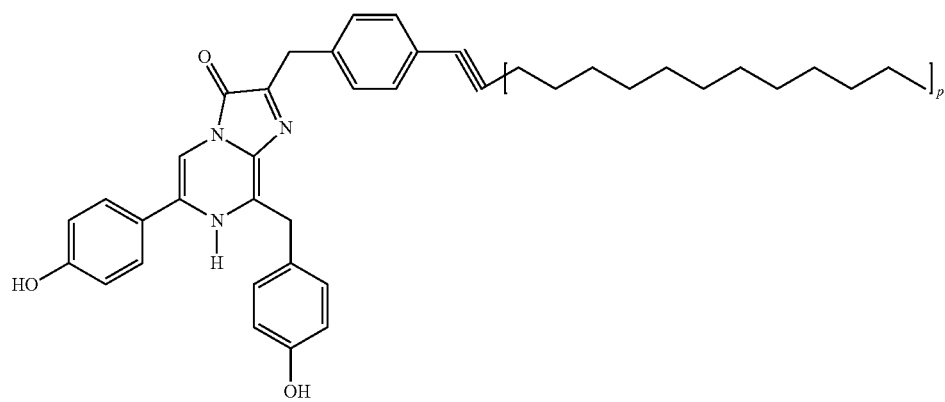

wherein p may be an integer ranging from 1 to 20, and Structure IV,

Structure IV

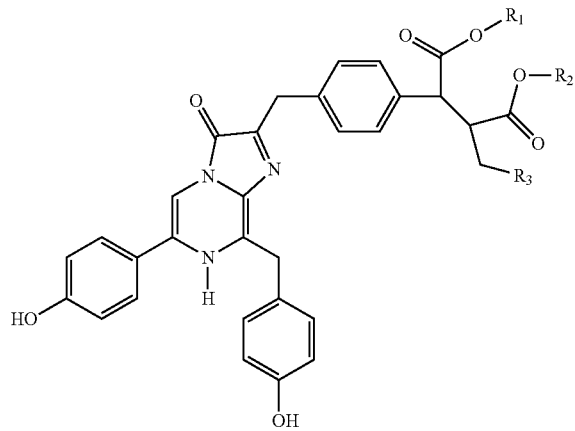

wherein R1, R2, and R3 are independently alkyl, optionally substituted alkyl, alkenyl, or aralkyl; and visualizing and/or imaging said subject or one or more portions thereof.

18. A method of examining an animal, avian or human object, comprising the steps of:

perfusing, administering, injecting, superfusing, infiltrating, or otherwise applying a bioluminescent generating system comprising a coelenterazine analog selected from the group consisting of Structure II, Structure II

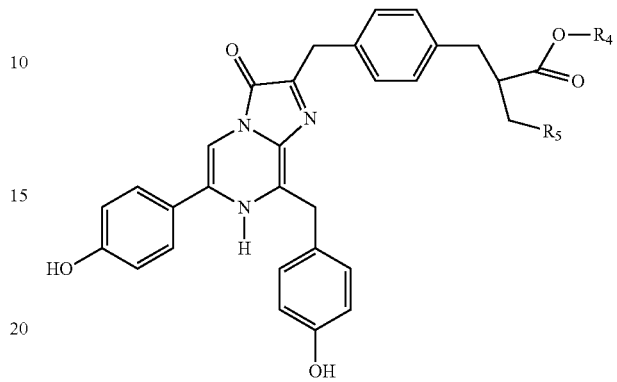

wherein R4 and R5 may independently be alkyl or aralkyl, and R4 may be aryl or optionally substituted aryl, aralkyl or optionally substituted aralkyl, and R5 may be alkyl, optionally substituted alkyl, alkoxy, aralkyl, or optionally substituted aralkyl, aryl, or a heterocycle, Structure III, Structure III

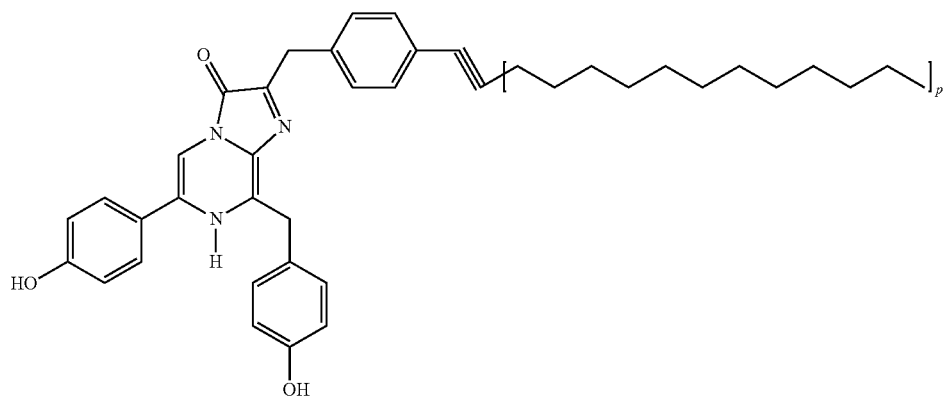

wherein p may be an integer ranging from 1 to 20, and Structure IV,

Structure IV

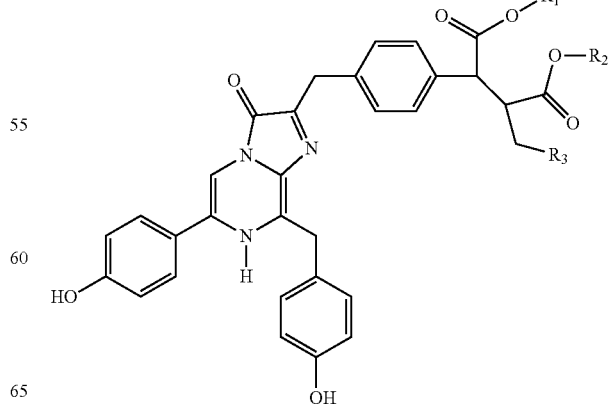

wherein R1, R2, and R3 are independently alkyl, optionally substituted alkyl, alkenyl, or aralkyl, to a selected animal, avian or human object to be examined to provide bioluminescent illumination to said object;

obtaining one or images of said object with bioluminescent illumination with a camera system sensitive to the wavelength of emission of the bioluminescent generating system.

19. The method of claim 18, wherein said one or more images are obtained in dim visible light conditions.

20. The method of claim 18, wherein said one or more images are color or monochrome images.

21. The method of claim 18, further comprising obtaining one or more images of said object with visible light illumination, said visible light comprising visible light in a wavelength range which does not include light in a wavelength range of light emitted by the bioluminescent generating system.

22. The method of claim 21, wherein said images are obtained with a camera system sensitive to the wavelength of emission of the visible light illumination.

* * * * *